United States Patent [19]

Krumkalns et al.

[11] Patent Number: 4,552,960

[45] Date of Patent: Nov. 12, 1985

[54] FUNGICIDAL AMINES

[75] Inventors: Eriks V. Krumkalns, Indianapolis; David L. Smiley, Greenfield, both of Ind.

[73] Assignee: Eli Lilly and Company, Indianapolis, Ind.

[21] Appl. No.: 595,866

[22] Filed: Apr. 2, 1984

Related U.S. Application Data

[63] Continuation-in-part of Ser. No. 506,174, Jun. 20, 1983, abandoned.

[51] Int. Cl.$^4$ ............................................. C07D 241/20
[52] U.S. Cl. ..................................... 544/336; 546/296; 546/300; 546/304; 546/312; 546/333; 546/334
[58] Field of Search ................ 544/336; 546/296, 300, 546/304, 312, 333, 334; 424/250, 245

[56] References Cited

U.S. PATENT DOCUMENTS

| | | | |
|---|---|---|---|
| 2,965,646 | 12/1960 | Gardner et al. | 260/296 |
| 3,784,574 | 1/1974 | Maravetz | 260/347.7 |
| 3,920,651 | 11/1975 | Ecsery et al. | 260/256.4 |
| 3,960,886 | 6/1976 | Schulenberg | 260/326.5 |
| 4,054,655 | 10/1977 | Donald | 424/250 |
| 4,293,552 | 10/1981 | Miesel | 544/336 |
| 4,359,576 | 11/1982 | Tenhaken et al. | 544/336 |

FOREIGN PATENT DOCUMENTS

| | | |
|---|---|---|
| 0000816 | 2/1979 | European Pat. Off. |
| 7039256 | 5/1967 | Japan |
| 2056974 | 3/1981 | United Kingdom ................. 237/20 |

OTHER PUBLICATIONS

Hauser et al., *J. Org. Chem.*, 14, 310, (1949).
Phillips, *J. Am. Chem. Soc.*, 78, 4441, (1956).
Profft, *J. Prakt. Chem.*, 4, 19, (1956).
Chemical Abstracts 51:5074a.
Magnus et al., *J. Am. Chem. Soc.*, 78, 4127, (1956).
Chemical Abstracts 52:2011h.
Chemical Abstracts 60:9239h.
Singerman et al., *J. Het. Chem.*, 3, 151, (1964).
Matsukawa et al., *J. Pharm. Soc. Japan*, 71, 895, (1951).
Chemical Abstracts 46:8122(c).
Winternitz et al., *Bull. Soc. Chim. France*, 646, (1952).
Chemical Abstracts 47:12269a.
Gardner et al., *J. Med. Pharm. Chem.*, 3, 461, (1961).
Steinhauser et al., *J. Prakt. Chem.*, 93, 387, (1916).
Chemical Abstracts 10:1639.
Behun et al., *J. Org. Chem.*, 26, 4981, (1961).
Gerns et al., *J. Med. Chem.*, 9 (1), 108, (1966).
Clark-Lewis et al., *J. Chem. Soc.*, 5556, (165).

*Primary Examiner*—John Kight
*Assistant Examiner*—M. L. Moore
*Attorney, Agent, or Firm*—Bruce J. Barclay; Kathaleen S. Page; Arthur R. Whale

[57] ABSTRACT

N,N-Disubstituted heterocyclic amines are useful as fungicides.

21 Claims, No Drawings

FUNGICIDAL AMINES

This is a continuation-in-part of Ser. No. 506,174, filed June 20, 1983, now abandoned.

SUMMARY OF THE INVENTION

The present invention relates to a method for controlling the growth of fungal diseases which comprises applying to the locus of the plant for which control is desired a disease inhibiting and non-herbicidal amount of a compound of the formula

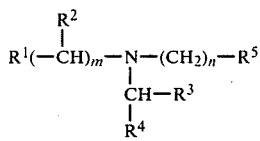

wherein:

$R^1$ is

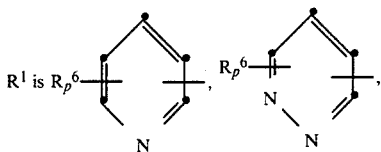

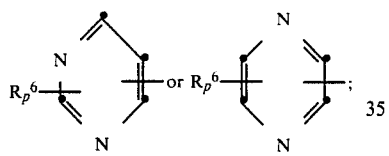

$R^2$ is hydrogen, $C_1$-$C_6$ alkyl, phenyl or phenyl monosubstituted with $C_1$-$C_4$ alkyl, $C_1$-$C_4$ alkoxy, halogen, $C_1$-$C_4$ haloalkyl or $C_1$-$C_4$ haloalkoxy;

$R^3$ is hydrogen or phenyl;

$R^4$ is hydrogen, $C_1$-$C_{12}$ alkyl, $C_1$-$C_{10}$ haloalkyl, $C_2$-$C_{10}$ alkenyl, $C_2$-$C_{10}$ alkynyl,

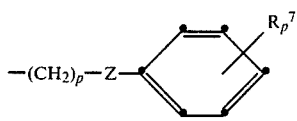

$C_3$-$C_8$ cycloalkyl, 1,3-dioxyl or naphthalenyl;

$R^5$ is

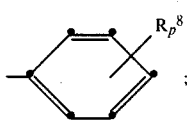

$R^6$ is $C_1$-$C_4$ alkyl, $C_1$-$C_4$ alkoxy, halogen, $C_1$-$C_4$ haloalkyl or $C_1$-$C_4$ haloalkoxy;

$R^7$ is $C_1$-$C_4$ alkyl, $C_1$-$C_4$ alkoxy, $C_1$-$C_4$ alkylthio, halogen, $C_1$-$C_4$ haloalkyl or $C_1$-$C_4$ haloalkoxy;

$R^8$ is $C_1$-$C_4$ alkyl, $C_1$-$C_4$ alkoxy, $C_1$-$C_4$ alkylthio, halogen, $C_1$-$C_4$ haloalkyl, $C_1$-$C_4$ haloalkoxy or

Q is O, S or a direct link;
Z is O, S, —CH=CH— or a direct link;
m is 0, 1 or 2;
n is 0, 1, 2 or 3;
each p is 0, 1 or 2;
with the proviso that m and n are not simultaneously 0;
and the agronomically acceptable salts thereof.

The present invention also relates to a compound of the formula

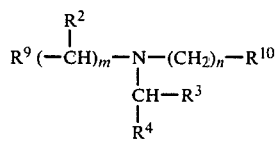

wherein $R^2$ is hydrogen, $C_1$-$C_6$ alkyl, phenyl or phenyl monosubstituted with $C_1$-$C_4$ alkyl, $C_1$-$C_4$ alkoxy, halogen, $C_1$-$C_4$ haloalkyl or $C_1$-$C_4$ haloalkoxy;

$R^3$ is hydrogen or phenyl;

$R^4$ is hydrogen, $C_1$-$C_{12}$ alkyl, $C_1$-$C_{10}$ haloalkyl, $C_2$-$C_{10}$ alkenyl, $C_2$-$C_{10}$ alkynyl,

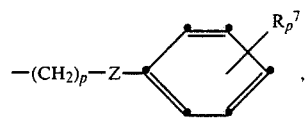

$C_3$-$C_8$ cycloalkyl, 1,3-dioxyl or naphthalenyl;

$R^6$ is $C_1$-$C_4$ alkyl, $C_1$-$C_4$ alkoxy, halogen, $C_1$-$C_4$ haloalkyl or $C_1$-$C_4$ haloalkoxy;

$R^7$ is $C_1$-$C_4$ alkyl, $C_1$-$C_4$ alkoxy, $C_1$-$C_4$ alkylthio, halogen, $C_1$-$C_4$ haloalkyl or $C_1$-$C_4$ haloalkoxy;

$R^9$ is

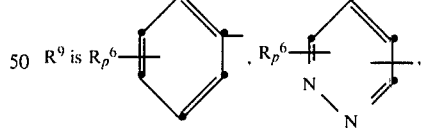

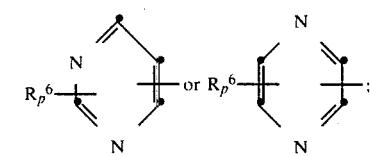

$R^{10}$ is

$R^{11}$ is $C_1$–$C_4$ alkyl, $C_1$–$C_4$ alkylthio, halogen, $C_1$–$C_4$ haloalkyl, $C_1$–$C_4$ haloalkoxy or

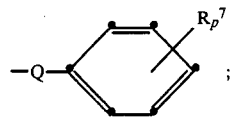

Q is O, S or a direct link;
Z is O, S, —CH=CH— or a direct link;
m is 0, 1 or 2;
n is 0, 1, 2 or 3;
each p is 0, 1 or 2;
q is 1 or 2;
with the proviso that m and n are not simultaneously 0;
and the agronomically acceptable salts thereof. Compositions containing the novel compounds are also taught and claimed.

DETAILED DESCRIPTION OF THE INVENTION

In the above formula, $C_1$–$C_{12}$ alkyl includes methyl, ethyl, n-propyl, isopropyl, n-butyl, sec.-butyl, isobutyl, t-butyl, n-pentyl, isopentyl, sec.-pentyl, neopentyl, n-hexyl, sec.-hexyl, isohexyl, n-heptyl, isoheptyl, sec.-heptyl, n-octyl, sec.-octyl, isooctyl, n-nonyl, sec.-nonyl, isononyl, n-decyl, sec.-decyl, and the like.

$C_2$–$C_{10}$ Alkenyl is a $C_2$–$C_{10}$ chain containing one carbon-carbon double bond. Such $C_2$–$C_{10}$ alkenyl groups include vinyl, allyl, 1-butenyl, isobutenyl, 3,3-dimethyl-1-butenyl, 4-methyl-2-pentenyl, 4-heptenyl, 3-octenyl, 5-decenyl, and the like.

$C_2$–$C_{10}$ Alkynyl represents a straight chain or branched carbon chain having from two to ten carbon atoms and one or more carbon-carbon triple bonds. Such $C_2$–$C_{10}$ alkynyl groups include ethynyl, propynyl, 1-butynyl, 2-pentynyl, 2-octynyl and the like.

$C_3$–$C_8$ Cycloalkyl represents saturated monocyclic cycloalkyl groups such as cyclopropyl, cyclobutyl, cyclopentyl, cyclohexyl, cycloheptyl, and cyclooctyl.

$C_1$–$C_4$ Alkoxy includes methoxy, ethoxy, n-propoxy and the like.

$C_1$–$C_4$ Alkylthio includes methylthio, ethylthio, n-propylthio, isopropylthio, t-butylthio, and the like.

The terms "halogen" or "halo" represent fluorine, chlorine, bromine and iodine.

$C_1$–$C_{10}$ Haloalkyl is a $C_1$–$C_{10}$ alkyl group bearing one or more halogen substituents. Such haloalkyl groups include trifluoromethyl, pentafluoroethyl, 1-iodo-2,2,2-trifluoroethyl, 3-chloropropyl, 2-iodopropyl, 2-fluoro-2-methylpropyl, 1-iodobutyl, 4-chloropentyl, 3-fluorohexyl, 3-fluorooctyl, 6-chlorodecyl and the like. $C_1$–$C_6$ haloalkyl is preferred.

$C_1$–$C_4$ Haloalkoxy includes trifluoromethoxy, 1-bromoethoxy, 1,1,2,2-tetrafluoroethoxy, 2,2,2-trifluoroethoxy, pentafluoroethoxy, and the like.

Pyridyl represents 2-, 3- or 4-pyridyl; pyrimidyl represents 2-, 4- or 5-pyrimidyl; pyrazyl represents 2-pyrazyl; and pyridazyl represents 3-or 4-pyridazyl.

Agronomically acceptable salts provided by this invention include both acid addition salts such as hydrochlorides, hydroiodides, hydrobromides and the like, and quaternary ammonium salts such as methyl iodides, ethyl iodides, and methyl bromides.

Preferred compounds have the above formula wherein $R^1$ is pyridyl and m is 1. Especially preferred compounds have the above formula wherein $R^1$ is 3-pyridyl.

The compounds of the present invention may be prepared by procedures well known to those skilled in the art. The preferred synthetic process involves alkylating the disubstituted amine starting material or its alkali metal derivative with an appropriately substituted alkyl halide to give a compound of the invention. The scheme for this reaction is as follows.

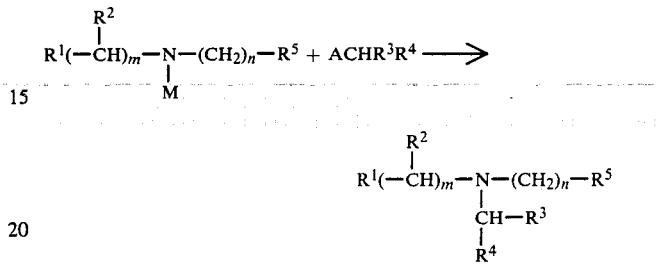

wherein $R^1$, $R^2$, $R^3$, $R^4$, $R^5$, m and n are as defined above, A is halogen and M is hydrogen or an alkali metal such as potassium, lithium or sodium.

This reaction is performed using standard alkylation techniques which are well known to those skilled in the art. For example, this reaction can be carried out by combining the disubstituted amine with about an equimolar to a slight excess quantity of the alkylating agent in a mutual solvent such as tetrahydrofuran, diethyl ether, dichloromethane, dioxane, dimethylsulfoxide, dimethylformamide, benzene, toluene and the like. A preferred aspect of this reaction involves the addition of a suitable base of sufficient strength to extract the proton on the disubstituted amine starting material. Suitable bases include potassium hydride, lithium hydride, sodium hydride and the like. Typically approximately 1 to 5 equivalents of the base are added to the reaction mixture. The reaction generally is substantially complete after about 2 to about 200 hours when carried out at a temperature of about 20° C. to about 200° C., preferably from about 25° C. to 75° C. The product of the reaction may be isolated by simply removing the reaction solvent, for instance by evaporation under reduced pressure. The residue is then typically dissolved into a water immiscible organic solvent, the solution washed with water and concentrated under vacuum. The amine thus formed may be further purified if needed by any of several routine methods including crystallization from common solvents, chromatography over solid supports such as silica or alumina, and related purification techniques.

Compounds of the present invention may be prepared by methods employing known starting materials that are readily available. The disubstituted amines that are employed as starting materials can be prepared by reacting an appropriately substituted amine with a carbonyl derivative to form a Schiff Base and then reducing the Schiff Base by known procedures, preferably by a palladium on carbon catalyzed hydrogenation reaction or by using sodium borohydride in alcohol. The disubstituted amine starting material may also be prepared by alkylating a primary amine with a halogen derivative again according to standard procedures. The schemes for these reactions are as follows.

When n is other than 0 in the above formula, the disubstituted amine starting material may be synthesized by the following process:

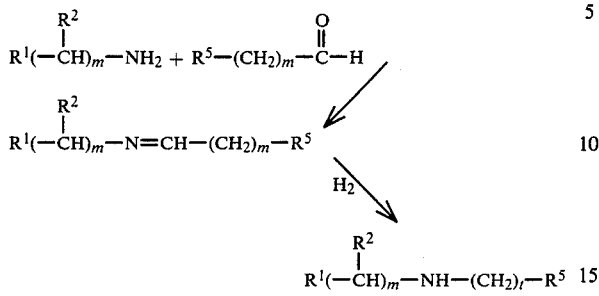

wherein $R^1$, $R^2$, $R^5$ and m are as defined above and t is 1, 2 or 3.

When m is other than 0, the starting material may be prepared by the following procedure:

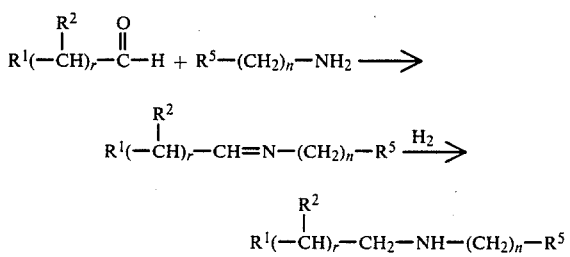

wherein $R^1$, $R^2$, $R^5$ and n are as defined above, and r is 0 or 1.

The scheme for the alkylation reaction is as follows:

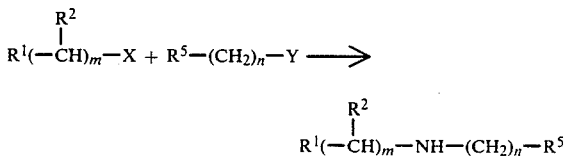

wherein $R^1$, $R^2$, $R^5$, m and n are as defined above, and one of X and Y is amino and the other is a good leaving group such as halogen, with the proviso that when m is 0, X is amino, and when n is 0, Y is amino.

The disubstituted amine starting materials can also be prepared by combining a ketone with an appropriately substituted amine to form the Schiff base, which can then be reduced by standard procedures to provide the corresponding compound. The reaction scheme for this process is as follows:

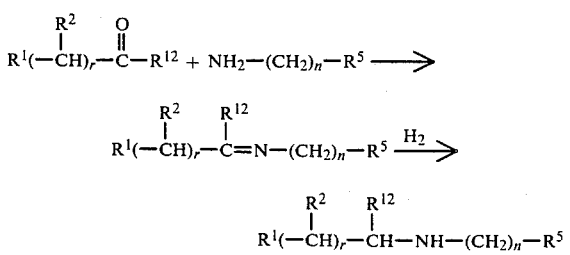

wherein $R^1$, $R^2$, $R^5$, n and r are as defined above and $R^{12}$ is $C_1$-$C_6$ alkyl, phenyl, or phenyl monosubstituted with $C_1$-$C_4$ alkyl, $C_1$-$C_4$ alkoxy, halogen, $C_1$-$C_4$ haloalkyl or $C_1$-$C_4$ haloalkoxy. Starting materials wherein $R^{12}$ is substituted or unsubstituted phenyl are preferably prepared by this process according to the general conditions outlined above.

An alternative procedure for preparing disubstituted amine starting materials wherein at least one of $R^2$ is other than hydrogen involves combining an aldehyde with an appropriately substituted amine to give the Schiff Base which can then be reacted with a lithium compound to provide the starting material as desired. This reaction scheme is as follows:

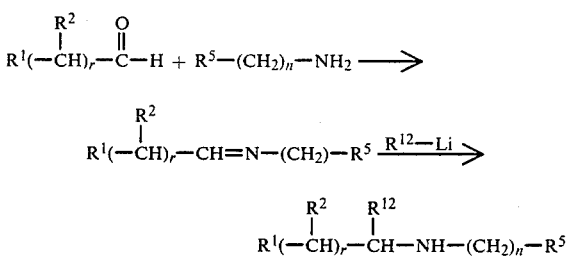

The reaction of the lithium reagent with the imine is typically performed under inert conditions and at a temperature between about $-80°$ C. and $20°$ C. The reaction is typically complete after about 1 to 24 hours and the product may be isolated by standard conditions.

Because all the compounds comprehended by this invention are amines, the compounds are basic in nature and readily form salts at the amine nitrogen atom. The salt moiety may also form at the nitrogen atom in the $R^1$ substituent as defined above. However, the present compounds are not limited by the position on the compound where the salt is formed, as the present invention includes all salts regardless of the form they take. The salts are typically formed by reacting a compound of the invention with an equimolar or an excess amount of acid or lower alkyl alkylating agent. The reactants are generally combined in a mutual solvent such as diethyl ether or benzene and the salt normally precipitates out of solution within about 1 hour to 10 days and can be isolated by filtration.

The following detailed Examples are provided in an effort to more fully illustrate specific aspects of this invention. The Examples are not intended to be limiting in any respect and should not be so construed. In addition to the given physical data, infrared spectroscopy (IR) was performed for certain of these compounds as well. Each compound's structure was verified by nuclear magnetic resonance (NMR).

EXAMPLE 1

N-Butyl-N-[(4-chlorophenyl)methyl]-(5-pyrimidyl)amine

A. N-[(4-Chlorophenyl)methyl]-(5-pyrimidyl)imine

To a solution of 7 g of 4-chlorobenzaldehyde and 5 g of 5-aminopyrimidine dissolved in 250 ml of toluene was added a catalytic amount of p-toluenesulfonic acid. The reaction mixture was refluxed for approximately 16 hours and the water formed as a by-product of the reaction was collected with a Dean Stark trap. The solution was filtered hot and the filtrate was concentrated under vacuum. The residue was washed with deithyl ether and Skellysolve B and the solids were dried to afford 9 g of N-[(4-chlorophenyl)methyl]-(5-pyrimidyl)imine. mp=140°-141° C.

Analysis calculated for $C_{11}H_8ClN_3$: Theory: C, 60.70; H, 3.70; N, 19.31; Found: C, 60.97; H, 3.55; N, 19.07.

B. N-[(4-Chlorophenyl)methyl]-(5-pyrimidyl)amine

To a solution of 7 g of N-[(4-chlorophenyl)methyl]-(5-pyrimidyl)imine dissolved in 250 ml of methanol was added 4 g of sodium borohydride. The reaction mixture was stirred overnight at room temperature and then concentrated under vacuum. The residue was dissolved in dichloromethane and washed with water. The organic phase was separated, dried over anhydrous magnesium sulfate, filtered and concentrated. The residue was washed with Skellysolve B and diethyl ether and dried to provide 4 g of N-[(4-chlorophenyl)methyl]-(5-pyrimidyl)amine. mp=121° C.

C. To a solution of 2.2 g of N-[(4-chlorophenyl)methyl]-(5-pyrimidyl)amine dissolved in 50 ml of tetrahydrofuran was added 2 g of a 24.6% suspension of potassium hydride in oil. The reaction was allowed to stir at room temperature for approximately 1 hour at which time 2 g of iodobutane was added to the reaction mixture. The mixture was stirred at room temperature overnight and concentrated under reduced pressure. The residue was dissolved in diethyl ether and the organic phase was washed with water, separated and dried over anhydrous magnesium sulfate. Following concentration of the solution under reduced pressure the residue was chromatographed over silica gel. Fractions containing the major component were combined and the solvent was evaporated therefrom to afford N-butyl-N-[(4-chlorophenyl)methyl]-(5-pyrimidyl)amine as a solid. mp=67°-68° C.

Analysis calculated for $C_{15}H_{18}ClN_3$: Theory: C, 65.33; H, 6.58; N, 15.24; Found: C, 65.04; H, 6.31; N, 15.25.

EXAMPLE 2

N-(2-Butenyl)-N-[(4-chlorophenyl)methyl]-(3-pyridyl)amine

A. N-[(4-Chlorophenyl)methyl]-(3-pyridyl)imine

To a solution of 30 g of 3-aminopyridine and 42 g of 4-chlorobenzaldehyde dissolved in 500 ml of toluene was added a small amount of p-toluenesulfonic acid. The reaction mixture was refluxed for approximately 6 hours and the water formed was collected with a Dean Stark trap. The reaction mixture was filtered hot and the filtrate was allowed to cool overnight. The filtrate was concentrated under vacuum and the residue was washed with diethyl ether and Skellysolve B. The solids were collected by filtration to provide 62 g of N-[(4-chlorophenyl)methyl]-(3-pyridyl)imine.

B. N-[(4-Chlorophenyl)methyl]-(3-pyridyl)amine

To a solution of 40 g of N-[(4-chlorophenyl)methyl]-(3-pyridyl)imine dissolved in 400 ml of methanol was added 12 g of sodium borohydride portionwise while maintaining the temperature of the reaction mixture below 50° C. The reaction mixture was allowed to stir at room temperature overnight whereupon the reaction mixture was evaporated to dryness. The residue was dissolved in water and diethyl ether and the organic phase was separated and dried over anhydrous magnesium sulfate. The filtrate was concentrated under vacuum and the residue was recrystallized from diethyl ether/Skellysolve B in afford 38 g of N-[(4-chlorophenyl)methyl]-(3-pyridyl)amine. mp=107°-108° C.

Analysis calculated for $C_{12}H_{11}ClN_2$: Theory: C, 65.91; H, 5.07; N, 12.81; Found: C, 66.19; H, 4.92; N, 12.96.

C. A solution of 4.4 g of N-[(4-chlorophenyl)methyl]-(3-pyridyl)amine dissolved in 50 ml of tetrahydrofuran was added to a suspension of 4 g of a 24.6% suspension of potassium hydride in oil in tetrahydrofuran. The mixture was allowed to stir at room temperature for approximately 30 minutes whereupon 4 g of 1-bromo-2-butene was added dropwise to the reaction mixture. The mixture was allowed to stir at room temperature overnight at which time the solution was evaporated to dryness. The residue was dissolved in dichloromethane and washed with water. The organic phase was dried over anhydrous magnesium sulfate, filtered and concentrated under vacuum. The oil residue was chromatographed over silica gel. Fractions containing the major component were combined and the solvent was evaporated therefrom to provide 3 g of N-(2-butenyl)-N-[(4-chlorophenyl)methyl]-(3-pyridyl)amine as an oil.

EXAMPLE 3

N-Butyl-N-[(4-chlorophenyl)methyl]-[2-(4-methylpyridyl)]amine

A solution of 4.6 g of N-[(4-chlorophenyl)methyl]-[2-(4-methylpyridyl)]amine dissolved in 100 ml of tetrahydrofuran was added to a solution of 4 g of a 24.6% suspension of potassium hydride in oil in tetrahydrofuran. Four grams of iodobutane was added and the reaction mixture was allowed to stir at room temperature overnight, whereupon toluene was added to the solution. The organic phase was separated, dried over anhydrous magnesium sulfate and concentrated under reduced pressure. The oil residue was chromatographed over silica gel while eluting with toluene and acetone. Fractions containing the major component were combined and the solvent was evaporated therefrom to provide 4 g of N-butyl-N-[(4-chlorophenyl)methyl]-[2-(4-methylpyridyl)]amine as an oil.

Analysis calculated for $C_{17}H_{21}ClN_2$: Theory: C, 70.70; H, 7.33; N, 9.70; Found: C, 70.46; H, 6.97; N, 9.78.

EXAMPLE 4

N-(Phenylmethyl)-N-[(2-chlorophenyl)methyl]-(pyrazyl)amine

A solution of 4.4 g of N-[(2-chlorophenyl)methyl]-pyrazineamine dissolved in tetrahydrofuran was added to a solution of 3.6 g of a 50.0% suspension of sodium hydride in oil in 25 ml of tetrahydrofuran under nitrogen. The reaction mixture was stirred for approximately 1 hour at room temperature and 2.6 ml of benzyl bromide in tetrahydrofuran was added dropwise. After approximately 2 hours, acetic acid was added to the reaction mixture and the solution was then poured into water and extracted with diethyl ether. The organic phase was washed with water and dried over magnesium sulfate. Following filtration the volatiles were removed under reduced pressure and the resulting oil residue was triturated with petroleum ether, filtered and dried to give 2.5 g of N-(phenylmethyl)-N-[(2-chlorophenyl)methyl]-(pyrazyl)amine. mp=74°-77° C.

Analysis calculated for $C_{18}H_{16}ClN_3$: Theory: C, 69.79; H, 5.21; N, 13.56; Found: C, 70.00; H, 5.42; N, 13.66.

EXAMPLE 5

N-(Phenylmethyl)-N-[(2-chlorophenyl)methyl]-(pyrazyl)amine monohydrochloride

Hydrochloric acid gas was bubbled through 250 ml of diethyl ether and this solution was added to a portion of the product formed in Example 4. A gum formed and the supernatant was decanted. The solids were washed with fresh diethyl ether and set aside. The solids were subsequently filtered and dried to give approximately 2.4 g of the hydrochloride salt. mp = 149°–152° C.

Analysis calculated for $C_{18}H_{17}Cl_2N_3$: Theory: C, 62.44; H, 4.95; N, 12.14; Found: C, 62.75; H, 5.03; N, 12.16.

The following Examples further illustrate compounds of the invention and were prepared by the general procedures outlined above.

EXAMPLE 6

N-Ethyl-N-(4-chlorophenyl)-[(3-pyridyl)methyl]amine oil

Analysis calculated for $C_{14}H_{15}ClN_2$: Theory: C, 68.15; H, 6.13; N, 11.35; Found: C, 68.30; H, 6.13; N, 11.11.

EXAMPLE 7

N-(Phenylmethyl)-N-(2,4-dichlorophenyl)-[(3-pyridyl)methyl]amine

Oil

Analysis calculated for $C_{19}H_{16}Cl_2N_2$: Theory: C, 66.48; H, 4.70; N, 8.16; Found: C, 66.27; H, 4.85; N, 8.15.

EXAMPLE 8

N-Methyl-N-(2-methyl-4-chlorophenyl)-[(3-pyridyl)methyl]amine

Oil

Analysis calculated for $C_{14}H_{15}ClN_2$: Theory: C, 68.15; H, 6.13; N, 11.35; Found: C, 68.26; H, 6.07; N, 11.23.

EXAMPLE 9

N-(Phenylmethyl)-N-(2-chlorophenyl)-[(3-pyridyl)methyl]amine

Oil

Analysis calculated for $C_{19}H_{17}ClN_2$: Theory: C, 73.90; H, 5.55; N, 9.07; Found: C, 73.70; H, 5.34; N, 8.90.

EXAMPLE 10

N-(2,4-Dichlorophenyl)-N-[(4-chlorophenyl)methyl]-[(3-pyridyl)methyl]amine

Oil

Analysis calculated for $C_{19}H_{15}Cl_3N_2$: Theory: C, 60.42; H, 4.00; N, 7.42; Found: C, 60.18; H, 4.14; N, 7.36.

EXAMPLE 11

N-(2,4-Dichlorophenyl)-N-(cyclohexylmethyl)[(3-pyridyl)methyl]amine

Oil

Analysis calculated for $C_{19}H_{22}Cl_2N_2$: Theory: C, 65.33; H, 6.35; N, 8.02; Found: C, 65.26; H, 6.40; N, 8.31.

EXAMPLE 12

N-Methyl-N-(2,4-dichlorophenyl)-[(3-pyridyl)methyl]amine

Oil

Analysis calculated for $C_{13}H_{12}Cl_2N_2$: Theory: C, 58.45; H, 4.53; N, 10.49; Found: C, 58.39; H, 4.69; N, 10.34.

EXAMPLE 13

N-Phenyl-N-[(4-chlorophenyl)methyl]-[(3-pyridyl)methyl]amine mp = 111°–112° C.

Analysis calculated for $C_{19}H_{17}ClN_2$: Theory: C, 73.90; H, 5.55; N, 9.07; Found: C, 73.68; H, 5.70; N, 8.92.

EXAMPLE 14

N-(4-Chlorophenyl)-N-[(4-chlorophenyl)methyl]-[(5-pyrimidyl)methyl]amine

Oil

EXAMPLE 15

N-(2-Propynyl)-N-(2,4-dichlorophenyl)-[(3-pyridyl)methyl]amine

Oil

Analysis calculated for $C_{15}H_{12}Cl_2N_2$: Theory: C, 61.87; H, 4.15; N, 9.62; Found: C, 61.67; H, 3.92; N, 9.88.

EXAMPLE 16

N-(4-Chlorophenyl)-N-(phenylmethyl)-[(2-pyridyl)methyl]amine

Oil

EXAMPLE 17

N-(Phenylmethyl)-N-[(2,4-dichlorophenyl)methyl]-(5-pyrimidyl)amine mp = 112°–115° C.

Analysis calculated for $C_{18}H_{15}Cl_2N_3$: Theory: C, 62.80; H, 4.39; N, 12.21; Found: C, 62.71; H, 4.66; N, 12.36.

EXAMPLE 18

N-(Phenylmethyl)-N-[(2,4-dichlorophenyl)methyl]-[(3-pyridyl)methyl]amine

Oil

EXAMPLE 19

N-(2,4-Dichlorophenyl)-N-[(1,3-diox-2-yl)methyl]-[(3-pyridyl)methyl]amine

Oil

Analysis calculated for $C_{17}H_{18}Cl_2N_2O_2$: Theory: C, 57.80; H, 5.14; N, 7.93; Found: C, 57.97; H, 5.29; N, 8.09.

EXAMPLE 20

N-(2,4-Dichlorophenyl)-N-(2-phenoxyethyl)[(3-pyridyl)methyl]amine

Oil

Analysis calculated for $C_{20}H_{18}Cl_2N_2O$: Theory: C, 64.35; H, 4.86; N, 7.50; Found: C, 64.39; H, 4.96; N, 7.59.

EXAMPLE 21

N-(Phenylmethyl)-N-(2-methyl-4-methoxyphenyl)[(3-pyridyl)methyl]amine

Oil

EXAMPLE 22

N-(2,4-Dichlorophenyl)-N-(naphthalenylmethyl)[(3-pyridyl)methyl]amine

Oil

Analysis calculated for $C_{23}H_{18}Cl_2N_2$: Theory: C, 70.24; H, 4.61; N, 7.12; Found: C, 70.48; H, 4.87; N, 6.86.

EXAMPLE 23

N-(4-Chlorophenyl)-N-(phenylmethyl)-[(3-pyridyl)methyl]amine mp=90°–92° C.

Analysis calculated for $C_{19}H_{17}ClN_2$: Theory: C, 73.90; H, 5.55; N, 9.07; Found: C, 73.75; H, 5.53; N, 8.89.

EXAMPLE 24

N-(2,4-Dichlorophenyl)-N-(diphenylmethyl)[(3-pyridyl)methyl]amine mp=113°–115° C.

Analysis calculated for $C_{25}H_{20}Cl_2N_2$: Theory: C, 71.60; H, 4.81; N, 6.68; Found: C, 71.42; H, 4.87; N, 6.42.

EXAMPLE 25

N-(Phenylmethyl)-N-(4-chlorophenyl)-[1-(3-pyridyl)ethyl]amine

Oil

Analysis calculated for $C_{20}H_{19}ClN_2$: Theory: C, 74.41; H, 5.93; N, 8.68; Found: C, 74.23; H, 5.87; N, 8.38.

EXAMPLE 26

N-Methyl-N-(4-chlorophenyl)-[1-(3-pyridyl)ethyl]amine

Oil

Analysis calculated for $C_{14}H_{15}ClN_2$: Theory: C, 68.15; H, 6.13; N, 11.35; Found: C, 68.42; H, 5.86; N, 11.43.

EXAMPLE 27

N-(Phenylmethyl)-N-(2,4-difluorophenyl)-[(3-pyridyl)methyl]amine

Oil

Analysis calculated for $C_{19}H_{16}F_2N_2$: Theory: C, 73.53; H, 5.20; N, 9.03; Found: C, 73.26; H, 4.96; N, 8.93.

EXAMPLE 28

N-Methyl-N-(4-chlorophenyl)-[(3-pyridyl)phenylmethyl]amine

Oil

Analysis calculated for $C_{19}H_{17}ClN_2$: Theory: C, 73.90; H, 5.55; N, 9.07; Found: C, 73.70; H, 5.40; N, 8.97.

EXAMPLE 29

N-(Phenylmethyl)-N-[(2,4-dichlorophenyl)methyl]-(2-pyrimidyl)amine mp=89°–91° C.

Analysis calculated for $C_{18}H_{15}Cl_2N_3$: Theory: C, 62.80; H, 4.39; N, 12.21; Found: C, 62.49; H, 4.40; N, 12.06.

EXAMPLE 30

N-Butyl-N-(2,4-dichlorophenyl)-[(3-pyridyl)methyl]amine

Oil

Analysis calculated for $C_{16}H_{18}Cl_2N_2$: Theory: C, 62.14; H, 5.83; N, 9.06; Found: C, 62.43; H, 5.95; N, 8.90.

EXAMPLE 31

N-Dodecyl-N-(2,4-dichlorophenyl)-[(3-pyridyl)methyl]amine

Oil

Analysis calculated for $C_{24}H_{34}Cl_2N_2$: Theory: C, 68.40; H, 8.13; N, 6.65; Found: C, 68.69; H, 8.35; N, 6.83.

EXAMPLE 32

N-Hexyl-N-(2,4-dichlorophenyl)-[(3-pyridyl)methyl]amine

Oil

Analysis calculated for $C_{18}H_{22}Cl_2N_2$: Theory: C, 64.10; H, 6.57; N, 8.31; Found: C, 63.83; H, 6.38; N, 8.08.

EXAMPLE 33

N-(2-Methylpropyl)-N-(2,4-dichlorophenyl)[(3-pyridyl)methyl]amine

Oil

Analysis calculated for $C_{16}H_{18}Cl_2N_2$: Theory: C, 62.15; H, 5.87; N, 9.06; Found: C, 61.90; H, 5.67; N, 8.93.

EXAMPLE 34

N-Butyl-N-(4-fluorophenyl)-[1-(3-pyridyl)ethyl]amine

Oil

Analysis calculated for $C_{17}H_{21}FN_2$: Theory: C, 74.97; H, 7.77; N, 10.29; Found: C, 74.15; H, 7.40; N, 9.60.

EXAMPLE 35

N-Butyl-N-(2-chlorophenyl)-[(3-pyridyl)methyl]amine

Oil

Analysis calculated for $C_{16}H_{19}ClN_2$: Theory: C, 69.93; H, 6.97; N, 10.19; Found: C, 69.95; H, 7.08; N, 10.02.

EXAMPLE 36

N-Butyl-N-(2,4-dimethylphenyl)-[(3-pyridyl)methyl]amine

Oil

Analysis calculated for $C_{18}H_{24}N_2$: Theory: C, 80.55; H, 9.01; N, 10.44; Found: C, 80.31; H, 9.28; N, 10.63.

EXAMPLE 37

N-(2-Butenyl)-N-(2,4-dichlorophenyl)-[(3-pyridyl)methyl]amine

Oil

Analysis calculated for $C_{16}H_{16}Cl_2N_2$: Theory: C, 62.55; H, 5.25; N, 9.12; Found: C, 62.22; H, 5.44; N, 9.09.

EXAMPLE 38

N-Methyl-N-(4-chlorophenyl)-[(3-pyridyl)methyl]amine

Oil

Analysis calculated for $C_{13}H_{13}ClN_2$: Theory: C, 67.10; H, 5.63; N, 12.04; Found: C, 66.98; H, 5.47; N, 11.86.

EXAMPLE 39

N-Butyl-N-[(4-chlorophenyl)methyl]-(pyrazyl)amine

Oil

Analysis calculated for $C_{15}H_{18}ClN_3$: Theory: C, 65.33; H, 6.58; N, 15.24; Found: C, 65.53; H, 6.79; N, 15.41.

EXAMPLE 40

N-(2-Methyl-2-propenyl)-N-(2,4-dichlorophenyl)-[(3-pyridyl)methyl]amine

Oil

Analysis calculated for $C_{16}H_{16}Cl_2N_2$: Theory: C, 62.55; H, 5.25; N, 9.12; Found: C, 62.56; H, 5.24; N, 9.19.

EXAMPLE 41

N-Butyl-N-(2-chlorophenyl)-[1-(3-pyridyl)pentyl]amine

Oil

Analysis calculated for $C_{20}H_{27}ClN_2$: Theory: C, 72.60; H, 8.22; N, 8.47; Found: C, 72.89; H, 8.35; N, 8.55.

EXAMPLE 42

N-Butyl-N-(4-chlorophenyl)-[(3-pyridyl)phenylmethyl]amine mp=76°–77° C.

Analysis calculated for $C_{22}H_{23}ClN_2$: Theory: C, 75.31; H, 6.61; N, 7.98; Found: C, 75.41; H, 6.61; N, 7.99.

EXAMPLE 43

N-(2-Propenyl)-N-(2,4-dichlorophenyl)-[(3-pyridyl)methyl]amine

Oil

Analysis calculated for $C_{15}H_{14}Cl_2N_2$: Theory: C, 61.45; H, 4.81; N, 9.55; Found: C, 61.28; H, 4.80; N, 9.69.

EXAMPLE 44

N-Butyl-N-[(2,4-dichlorophenyl)methyl]-[3-(2,6-dichloropyridyl)]amine

Oil

Analysis calculated for $C_{16}H_{16}Cl_4N_2$: Theory: C, 50.82; H, 4.27; N, 7.41; Found: C, 51.08; H, 4.38; N, 7.52.

EXAMPLE 45

N-(2-Butenyl)-N-(4-fluorophenyl)-[1-(3-pyridyl)ethyl]amine

Oil

Analysis calculated for $C_{17}H_{19}FN_2$: Theory: C, 75.53; H, 7.08; N, 10.36; Found: C, 75.23; H, 7.23; N, 10.11.

EXAMPLE 46

N-(3-Methyl-2-butenyl)-N-(2,4-dichlorophenyl)[(3-pyridyl)methyl]amine

Oil

Analysis calculated for $C_{17}H_{18}Cl_2N_2$: Theory: C, 63.56; H, 5.65; N, 8.72; Found: C, 63.70; H, 5.38; N, 8.50.

EXAMPLE 47

N-(2-Butenyl)-N-(4-thiomethylphenyl)-[(3-pyridyl)methyl]amine

Oil

Analysis calculated for $C_{17}H_{20}N_2S$: Theory: C, 71.79; H, 7.09; N, 9.85; Found: C, 71.56; H, 6.94; N, 9.58.

EXAMPLE 48

N-(2-Butenyl)-N-(2-methyl-4-chlorophenyl)[(3-pyridyl)methyl]amine

Oil

Analysis calculated for $C_{17}H_{19}ClN_2$: Theory: C, 71.20; H, 6.68; N, 9.77; Found: C, 70.95; H, 6.81; N, 9.65.

EXAMPLE 49

N-(3-Phenyl-2-propenyl)-N-(2,4-dichlorophenyl)-[(3-pyridyl)methyl]amine

Oil

Analysis calculated for $C_{21}H_{18}Cl_2N_2$: Theory: C, 68.30; H, 4.91; N, 7.59; Found: C, 68.37; H, 5.11; N, 7.38.

EXAMPLE 50

N-(2-Butenyl)-N-(3,4-dichlorophenyl)-[(3-pyridyl)methyl]amine

Oil

Analysis calculated for $C_{16}H_{16}Cl_2N_2$: Theory: C, 62.55; H, 5.25; N, 9.12; Found: C, 62.36; H, 5.22; N, 8.89.

EXAMPLE 51

N-(2-Butenyl)-N-[(2,4-dichlorophenyl)methyl]-(pyrazyl)amine

Oil

Analysis calculated for $C_{15}H_{15}Cl_2N_3$: Theory: C, 58.46; H, 4.91; N, 13.63; Found: C, 58.39; H, 4.88; N, 13.45.

EXAMPLE 52

N-(Cyclopropylmethyl)-N-(2,4-dichlorophenyl)[(3-pyridyl)methyl]amine

Oil

Analysis calculated for $C_{16}H_{16}Cl_2N_2$: Theory: C, 62.55; H, 5.25; N, 9.12; Found: C, 62.38; H, 5.10; N, 9.12.

EXAMPLE 53

N-butyl-N-(2,4-dichlorophenyl)-[(3-pyridinium)methyl]amine methyl iodide mp=81°–84° C.

Analysis calculated for $C_{17}H_{21}Cl_2IN_2$: Theory: C, 45.26; H, 4.69; N, 6.21; Found: C, 45.11; H, 4.58; N, 6.00.

EXAMPLE 54

N-(4-Chlorobutyl)-N-(2,4-dichlorophenyl)-[(3-pyridyl)methyl]amine

Oil

Analysis calculated for $C_{16}H_{17}Cl_3N_2$: Theory: C, 55.92; H, 4.99; N, 8.15; Found: C, 56.02; H, 4.88; N, 8.16.

EXAMPLE 55

N-Butyl-N-(4-chlorophenyl)-[(3-pyridyl)methyl]amine

Oil

Analysis calculated for $C_{16}H_{19}ClN_2$: Theory: C, 69.93; H, 6.97; N, 10.19; Found: C, 69.92; H, 7.08; N, 10.08.

EXAMPLE 56

N-Butyl-N-(4-chlorophenyl)-[(3-pyridyl)methyl]amine dihydrochloride mp=149°–152° C.

Analysis calculated for $C_{16}H_{21}Cl_3N_2$: Theory: C, 56.26; H, 6.09; N, 8.05; Cl, 30.59; Found: C, 55.33; H, 5.57; N, 7.86; Cl, 30.21.

EXAMPLE 57

N-Butyl-N-[4-(2,2,2-trifluoroethoxy)phenyl][(3-pyridyl)methyl]amine

Oil

Analysis calculated for $C_{18}H_{21}F_3N_2O$: Theory: C, 63.89; H, 6.26; N, 8.28; Found: C, 63.68; H, 6.47; N, 8.26.

The compounds of the present invention have been found to control plant fungal diseases. When employed in the treatment of such plant fungal diseases, the compounds are applied to the plants in a disease inhibiting and non-herbicidal amount. The term "disease inhibiting and non-herbicidal amount," as used herein, refers to an amount of a compound of the invention which kills or stunts the plant disease for which control is desired, but is not significantly toxic to the plant. This amount will generally be from about 1 to 1000 ppm, with 10 to 500 ppm being preferred. The exact concentration of compound required varies with the fungal disease to be controlled, the type formulation employed, the method of application, the particular plant species, climate conditions and the like.

The following experiments were performed in the laboratory to determine the fungicidal efficacy of the compounds of the invention.

EXPERIMENT 1

This initial screen was used to evaluate the efficacy of the present compounds against a variety of different agents causing plant diseases.

The test compounds were formulated for application by dissolving 48 mg of the compound into 1.2 ml of solvent. The solvent was prepared by mixing 100 ml of Tween 20 with 500 ml of acetone and 500 ml of ethanol. The solvent/compound solution was finally diluted to 120 ml with deionized water.

The formulated test compounds were applied by both soil drench and foliar methods. In the foliar spray application method the following plant pathogens and their corresponding host plants were employed.

| | |
|---|---|
| Powdery Mildew | Bean |
| Anthracnose | Cucumber |
| Rice Blast | Rice |
| Botrytis | Grape |
| Helminthosporium | Wheat |
| Leaf Rust | Wheat |
| Late Blight | Tomato |

The foliar application was conducted at a 400 ppm test compound concentration by either of two methods. In the botrytis test, the formulated compound was sprayed onto the plants with a small DeVilbiss atomizer at approximately 8 psi. In the remaining tests the formulated test compounds were sprayed by hand in an exhaust ventilated chamber. Single pots of different plant species were placed on raised, revolving pedestals in the chamber. Using a DeVilbiss spray gun, all test solutions were applied by hand at 40 psi. As the spray was delivered, the pedestals were rotated to expose all plant surfaces to the spray pattern. The spray was applied to past the run-off point. All treatments were allowed to dry and the host plants were inoculated with the pathogens 24 hours later.

In the soil drench application method the following plant pathogen and host plant were employed.

Rhizoctonia Damping-off-Cotton

The soil drench method was performed by uniformly syringing 20 ml of the formulation over the soil surface of each pot containing a different crop species. The pot size at the soil surface was 2.0 inches in diameter, thus equalling a test compound concentration of 35 lbs/acre (39.2 kg/ha).

The effectiveness of test compounds in controlling the foregoing plant diseases was rated on a scale of 1 to 5. On this scale "1" indicates severe disease (or no control), "2" is moderate disease, "3" is slight disease, "4" is very slight disease and "5" indicates no disease or 100% control. Also a phytotoxicity rating was recorded when apparent again using a scale from 1 to 5 wherein 1 indicates no toxicity and 5 indicates death to the plant. Finally, where phytotoxicity was present, a letter rating may be given to the plant indicating the type of injury caused to the plant. These injuries were coded as follows:

G=General necrosis
W=Wilting
S=Stunting
C=Chlorosis
F=Formative

Table 1 presents the activity of typical compounds of the present invention when evaluated in the foliar application method described above, while Table 2 presents the results of the soil drench application method.

TABLE 1

| | Foliar Application | | | | | | |
|---|---|---|---|---|---|---|---|
| Example No. of Compound Tested | Powdery Mildew | Anthracnose | Rice Blast | Botrytis | Helminthosporium | Leaf Rust | Late Blight |
| 1 | 3 | 1 | 4 | 1 | 4 | 5(3G) | 1 |
| 2 | 3 | 1 | 1 | 1 | 1 | 1 | 1 |
| 3 | 1 | 1 | 1 | 1 | 1 | 1 | 1 |

TABLE 1-continued

Foliar Application

| Example No. of Compound Tested | Powdery Mildew | Anthracnose | Rice Blast | Botrytis | Helminthosporium | Leaf Rust | Late Blight |
|---|---|---|---|---|---|---|---|
| 4 | 1 | 1 | 1 | 1 | 1 | 1 | 1 |
| 5 | 1 | 1 | 4 | 1 | 1 | 1 | 1 |
| 6 | 3 | 1 | 1 | 1 | 1 | 1 | 1 |
| 7 | 5 | 1 | 1 | 3 | 4 | 4(3G) | 1 |
| 8 | 3 | 1 | 1 | 1 | 1 | 1 | 1 |
| 9 | 5 | 1(3G) | 1 | 1 | 5 | 1 | 1 |
| 10 | 4(2F) | 1 | 1 | 3 | 4(3G) | 3 | 1 |
| 12 | 4 | 1 | 1 | 1 | 3 | 1 | 1 |
| 13 | 4(2F) | 1 | 1 | 1 | 1 | 1 | 1 |
| 15 | 5(3G) | 4 | 1 | 4 | 5 | 1 | 1 |
| 17 | 4 | 1 | 1 | 1 | 1 | 1 | 1 |
| 18 | 4 | 1 | 1 | 1 | 1 | 1 | 1 |
| 20 | 4 | 1 | 1 | 1 | 4 | 1 | 1 |
| 21 | 4 | 4 | 1 | 1 | 1 | 1 | 1 |
| 22 | 4 | 4 | 1 | 1 | 1 | 1 | 1 |
| 23 | 4 | 1 | 1 | 1 | 1 | 1 | 1 |
| 24 | 4(2G) | 1 | 1 | 1 | 1 | 1 | 1 |
| 25 | 4(2F) | 1 | 1 | 1 | 4 | 1 | 1 |
| 26 | 3 | 1 | 1 | 1 | 1 | 1 | 1 |
| 27 | 4 | 1 | 1 | 1 | 4 | 4 | 1 |
| 28 | 5(2G) | 1 | 1 | 1 | 5 | 1 | 1 |
| 29 | 1 | 1 | 1 | 1 | 1 | 1 | 1 |
| 30 | 5(2C) | 1 | 1 | 4 | 4 | 4 | 1 |
| 31 | 4(3G) | 1 | 1 | 1 | 1 | 1 | 1 |
| 32 | 5 | 1 | 1 | 3 | 4 | 3 | 1 |
| 33 | 5(2C) | 1 | 1 | 4 | 4 | 4 | 1 |
| 34 | 5 | 1 | 1 | 1 | 4 | 1 | 1 |
| 35 | 5 | 1 | 1 | 1 | 4 | 1 | 1 |
| 36 | 4(2C) | 1 | 1 | 1 | 1 | 1 | 1 |
| 37 | 5(2C) | 1 | 1 | 4 | 4 | 1 | 1 |
| 38 | 1 | 1 | 1 | 1 | 1 | 1 | 1 |
| 39 | 1 | 1 | 1 | 1 | 5 | 1 | 1 |
| 40 | 5(2G) | 1 | 1 | 3 | 5 | 1 | 1 |
| 41 | 5(2G) | 1(2G) | 1 | 1 | 1 | 1 | 1 |
| 42 | 5 | 1 | 1 | 1 | 1 | 3 | 1 |
| 44 | 1 | 1 | 1 | 1 | 1 | 1 | 1 |
| 45 | 1 | 1 | 1 | 1 | 4 | 1 | 1 |
| 46 | 5(3G) | 1 | 1 | 4 | 4 | 1 | 1 |
| 47 | 1 | 1 | 1 | 1 | 1 | 1 | 1 |
| 48 | 5 | 1 | 1 | 1 | 4 | 1 | 1 |
| 49 | 5 | 1 | 1 | 1 | 4 | 1 | 1 |
| 50 | 3(2G) | 1(3G) | —(5) | 1 | 1 | 1 | 1 |
| 51 | 1 | 1 | 1 | 1 | 4 | 1 | 1 |
| 52 | 5(2G) | 1 | 1 | 1 | 5 | 3 | 1 |
| 53 | 1 | 1(4G) | 1 | 1 | 4 | 1(2G) | 1 |
| 54 | 5 | 4 | 1 | 4 | 5 | 1 | 1 |

TABLE 2

Soil Drench Application

| Example No. of Compound Tested | Rhizoctonia |
|---|---|
| 1 | 3 |
| 2 | 3 |
| 3 | 1 |
| 4 | 1 |
| 5 | 1 |
| 6 | 1 |
| 7 | 4 |
| 8 | 1 |
| 9 | 3 |
| 10 | 1 |
| 12 | 3 |
| 13 | 1 |
| 15 | 1 |
| 17 | 1 |
| 18 | 1 |
| 20 | 1 |
| 21 | 1 |
| 22 | 1 |
| 23 | 1 |
| 24 | 1 |
| 25 | 4 |
| 26 | 1 |
| 27 | 3 |
| 28 | 4 |
| 29 | 1 |
| 30 | 4 |
| 31 | 1 |
| 32 | 1 |
| 33 | 4 |
| 34 | 4 |
| 35 | 1 |
| 36 | 3 |
| 37 | 3 |
| 38 | 1 |
| 39 | 4 |
| 40 | 4 |
| 41 | 1 |
| 42 | 1 |
| 44 | 1 |
| 45 | 1 |
| 46 | 4 |
| 47 | 1 |
| 48 | 4 |
| 49 | 1 |
| 50 | 1 |
| 51 | 1 |

TABLE 2-continued

Soil Drench Application

| Example No. of Compound Tested | Rhizoctonia |
| --- | --- |
| 52 | 1 |
| 53 | 1 |
| 54 | 1 |

EXPERIMENT 2

Compounds tested in this plant disease foliage screen were formulated in the same manner as described above for Experiment 1. The 400 ppm concentration obtained by this procedure was then serially diluted with water to obtain solutions having a lower concentration of test compound. The formulations were sprayed on the plants in the same manner as described above for foliar application. One day after treatment, the host plants were inoculated with the pathogen spores. The diseases and their corresponding host plants that were used in this experiment are as follows:

| | |
| --- | --- |
| Powdery mildew | Bean |
| Late blight | Tomato |
| Apple scab | Apple |
| Anthracnose | Cucumber |
| Rice blast | Rice |
| Downy mildew | Grape |
| Cercospora leafspot | Sugar beet |

After a suitable incubation period, when disease symptoms appeared on untreated control plants, treatments were rated for disease severity according to the rating system described above. The results are recorded in Table 3.

TABLE 3

| Example No. of Compound Tested | Concentration ppm | Powdery Mildew | Late Blight | Apple Scab | Anthracnose | Rice Blast | Downy Mildew | Cercospora |
| --- | --- | --- | --- | --- | --- | --- | --- | --- |
| 4 | 400 | 1 | 1 | 4 (2G) | 1 | 4 | 1 (2G) | 1 |
| | 100 | | | 1 (2G) | | 1 | | |
| | 25 | | | 1 | | 1 | | |
| 6 | 400 | 1 | 1 | | 1 (2G) | 1 | 3 | 1 |
| 7 | 400 | 5 (2C) | 1 | 5 | 1 | 1 | 1 | 4 |
| | 400 | 5 (2G) | | | | | | 5 |
| | 100 | 5 | | 4 | | | | 4 |
| | 100 | 4 | | | | | | |
| | 25 | 3 | | 3 | | | | 1 |
| | 25 | 4 | | | | | | |
| | 6 | 1 | | | | | | |
| 8 | 400 | 3 (2G) | 1 (2G) | | 1 | 1 | 5 | 1 |
| | 400 | | 4 | | | | 5 | |
| | 100 | | 1 | | | | 3 | |
| | 25 | | 1 | | | | 1 | |
| 9 | 400 | 5 | 1 | 3 | 1 | 1 | 3 | 1 |
| | 400 | 5 | 1 | 4 (2G) | 1 | 1 | 1 | 1 |
| | 400 | 5 (2C) | | | | | | |
| | 400 | 5 (3C) | | | | | | |
| | 100 | 4 | | 4 | | | | |
| | 100 | 3 | | | | | | |
| | 25 | 4 | | 1 | | | | |
| 9 | 25 | 4 | | 1 | | | | |
| | 25 | 3 | | | | | | |
| | 25 | 4 | | | | | | |
| | 6 | 1 | | | | | | |
| 10 | 400 | 5 (2G) | 1 | 1 | 1 | 3 | 1 | 4 |
| | 400 | 4 | | | | | | 4 |
| | 100 | 5 | | 1 | | | | |
| | 100 | 5 | | | | | | |
| | 25 | 5 | | 1 | | | | 1 |
| | 25 | 5 | | | | | | |
| | 6 | 3 | | | | | | |
| 12 | 400 | 4 | 1 | | 1 | 1 | 3 | 3 |
| | 400 | 4 | | 5 | | | | |
| | 100 | 3 | | 4 | | | | |
| | 25 | 1 | | 1 | | | | |
| 13 | 400 | 4 | 1 | | 1 | 1 | 1 | 1 |
| | 400 | 3 | | 1 | | | | |
| | 100 | 3 | | 1 | | | | |
| | 25 | 1 | | 1 | | | | |
| 17 | 400 | 5 | 1 | 1 | 1 | 1 | 1 | 1 |
| | 400 | 5 | | | | | | |
| | 100 | 1 | | | | | | |
| | 25 | 1 | | | | | | |
| 21 | 400 | 5 | 1 | 3 | 1 | 3 | 1 | 3 |
| | 400 | 5 | 4 | 3 | 4 | 3 | 1 | 1 |
| | 400 | 4 | | | | | | |
| | 100 | 5 | 1 | 1 | 4 | 1 | 1 | 1 |
| | 100 | 3 | | | | | | |
| | 100 | 3 | | | | | | |
| | 25 | 5 | 1 | 1 | 1 | 1 | 1 | 1 |
| | 25 | 1 | | | | | | |
| | 25 | 1 | | | | | | |
| | 6 | 1 | | | | | | |
| 22 | 400 | 5 (2F) | 1 | 1 | 1 | 1 | 1 | 1 |

TABLE 3-continued

| Example No. of Compound Tested | Concentration ppm | Powdery Mildew | Late Blight | Apple Scab | Anthracnose | Rice Blast | Downy Mildew | Cercospora |
|---|---|---|---|---|---|---|---|---|
|  | 100 | 4 | 1 | 1 | 1 | 1 | 1 | 1 |
|  | 25 | 1 | 1 | 1 | 1 | 1 | 1 | 1 |
| 23 | 400 | 3 | 3 | 1 | 1 (2G) | 1 | 3 | 1 |
|  | 100 | 1 | 1 | 1 | 1 | 1 | 1 | 1 |
|  | 25 | 1 | 1 | 1 | 1 | 1 | 1 | 1 |
| 24 | 400 | 5 | 1 | 1 | 1 | 3 |  |  |
|  | 400 | 5 |  |  |  | 4 |  |  |
|  | 100 | 5 |  |  |  | 1 |  |  |
|  | 100 | 5 |  |  |  |  |  |  |
|  | 25 | 5 |  |  |  | 1 |  |  |
|  | 25 | 4 |  |  |  |  |  |  |
|  | 6 | 4 |  |  |  |  |  |  |
| 25 | 400 | 4 (2F) | 1 | 1 | 1 | 4 | 1 | 1 |
|  | 400 | 4 |  |  |  | 3 |  |  |
|  | 100 | 1 |  |  |  | 1 |  |  |
|  | 25 | 1 |  |  |  | 1 |  |  |
| 26 | 400 | 3 | 1 | 4 (2G) | 1 | 4 | 1 | 3 |
|  | 400 |  |  | 3 (2G) |  | 1 |  |  |
|  | 100 |  |  | 1 |  | 1 |  |  |
|  | 25 |  |  | 1 |  | 1 |  |  |
| 30 | 400 | 5 | 5 | 3 | 1 | 1 | 1 | 1 |
|  | 400 | 4 | 1 | 4 | 1 | 1 | 1 | 4 |
|  | 400 | 5 |  |  |  |  |  |  |
|  | 100 | 4 | 1 | 3 | 1 | 1 | 1 | 3 |
|  | 100 | 3 |  |  |  |  |  |  |
|  | 100 | 5 |  |  |  |  |  |  |
|  | 100 | 5 |  |  |  |  |  |  |
| 30 | 25 | 4 | 1 | 3 | 1 | 1 | 1 | 1 |
|  | 25 | 5 |  |  |  |  |  |  |
|  | 25 | 3 |  |  |  |  |  |  |
|  | 6 | 1 |  |  |  |  |  |  |
|  | 6 | 4 |  |  |  |  |  |  |
| 31 | 400 | 5 | 1 | 1 | 1 | 1 | 1 | 1 |
|  | 400 | 5 (2C) |  |  |  |  |  |  |
|  | 100 | 5 |  |  |  |  |  |  |
|  | 25 | 4 |  |  |  |  |  |  |
|  | 6 | 3 |  |  |  |  |  |  |
| 32 | 400 | 5 | 1 | 1 | 1 | 1 | 1 | 5 |
|  | 400 | 5 (2C) |  |  |  |  |  | 4 |
|  | 100 | 5 |  |  |  |  |  | 3 |
|  | 100 | 5 |  |  |  |  |  |  |
|  | 25 | 4 |  |  |  |  |  | 1 |
|  | 25 | 1 |  |  |  |  |  |  |
|  | 6 | 3 |  |  |  |  |  |  |
| 33 | 400 | 5 | 1 | 3 | 1 | 1 | 1 | 1 |
|  | 400 | 4 |  |  |  |  |  |  |
|  | 100 | 4 |  |  |  |  |  |  |
|  | 100 | 3 |  |  |  |  |  |  |
|  | 25 | 4 |  |  |  |  |  |  |
|  | 6 | 1 |  |  |  |  |  |  |
| 36 | 400 | 5 | 1 | 1 | 1 | 1 | 1 | 1 |
|  | 400 | 4 |  |  |  |  |  |  |
|  | 100 | 3 |  |  |  |  |  |  |
|  | 25 | 1 |  |  |  |  |  |  |
| 37 | 400 | 5 | 1 | 1 | 1 | 1 | 4 | 5 |
|  | 400 | 5 |  |  |  |  | 1 | 4 |
|  | 100 | 4 |  |  |  |  | 1 | 4 |
|  | 100 | 4 |  |  |  |  |  | 1 |
|  | 25 | 1 |  |  |  |  | 1 | 3 |
|  | 25 | 1 |  |  |  |  |  | 1 |
|  | 6 | 1 |  |  |  |  |  | 1 |
| 38 | 400 | 1 | 3 |  | 1 | 1 | 1 | 1 |
| 39 | 400 | 1 | 1 | 4 | 1 | 1 | 3 | 1 |
| 40 | 400 | 1 | 1 | 1 | 1 | 1 | 1 | 5 |
|  | 400 |  |  |  |  |  |  | 4 |
|  | 100 |  |  |  |  |  |  | 1 |
|  | 25 |  |  |  |  |  |  | 1 |
| 42 | 400 | 5 | 1 | 1 | 1 | 1 | 1 | 1 |
|  | 400 | 4 |  |  |  |  |  |  |
|  | 100 | 4 |  |  |  |  |  |  |
|  | 100 | 3 |  |  |  |  |  |  |
|  | 25 | 3 |  |  |  |  |  |  |
|  | 25 | 4 |  |  |  |  |  |  |
|  | 6 | 1 |  |  |  |  |  |  |
| 43 | 400 | 5 | 1 | 5 | 1 | 1 | 1 | 4 |
|  | 400 | 4 |  | 4 |  |  |  | 1 |
|  | 100 | 3 |  | 4 |  |  |  | 1 |
|  | 25 | 1 |  | 1 |  |  |  | 1 |
| 44 | 400 | 1 | 1 | 3 | 1 | 1 | 1 | 1 |

TABLE 3-continued

| Example No. of Compound Tested | Concentration ppm | Powdery Mildew | Late Blight | Apple Scab | Anthracnose | Rice Blast | Downy Mildew | Cercospora |
|---|---|---|---|---|---|---|---|---|
| 47 | 400 | 1 | 1 | 3 | 4 | 1 | 1 | 1 |
| 50 | 400 | 1 | 1 | 3 | 1 | 1 | 1 | 1 |

EXPERIMENT 3

Certain of the compounds provided by this invention were tested in an effort to evaluate their fungicidal efficacy and systemic control of various cereal grain diseases. The compounds tested were formulated as above and applied by both foliar spray and soil drench methods. The diseases and host plants employed in this test were as follows.

| | |
|---|---|
| Powdery mildew | Wheat |
| Leaf rust | Wheat |
| Helminthosporium leaf spot | Wheat |
| Septoria leaf blotch | Wheat |

After a suitable incubation period when disease symptoms had appeared on untreated plants, treatments were rated for disease severity. The compounds were rated as above, and the results of the foliar test appear in Table 4, while the results of the soil drench test are presented in Table 5.

TABLE 4

| Example No. of Compound Tested | Concentration ppm | Foliar Application | | | |
|---|---|---|---|---|---|
| | | Powdery Mildew | Leaf Rust | Helminthosporium | Septoria |
| 1 | 400 | 1 | 3 | 1 | 1 |
| 2 | 400 | 1 | 1 | 1 (2C) | 1 |
| 3 | 400 | 1 | 1 | 1 | 1 |
| 4 | 400 | 5 | 1 | 1 | 1 |
| | 400 | 1 | | | |
| | 100 | 1 | | | |
| | 25 | 1 | | | |
| 5 | 400 | 4 | 1 | 1 | 4 |
| | 400 | 4 | | | 1 |
| | 100 | 4 | | | 1 |
| | 25 | 3 | | | 1 |
| 6 | 400 | 1 | 1 | 1 | 1 |
| 7 | 400 | 5 | 4 (2C) | 4 | 5 |
| | 400 | 5 | 4 | 4 | 5 |
| | 100 | 5 | 3 | 5 (2G) | 5 |
| | 100 | 4 | 3 | 3 | 5 |
| | 25 | 5 | 3 | 4 | 5 |
| | 25 | 1 | 1 | 1 | 5 |
| | 6 | 1 | 1 | 1 | 3 |
| 8 | 400 | 4 | 1 | 1 | 1 |
| | 400 | 4 | | | |
| | 100 | 1 | | | |
| | 25 | 1 | | | |
| 9 | 400 | 5 | 3 | 5 (2G) | 5 |
| | 400 | 1 | 1 | 5 | 5 |
| | 100 | 1 | 1 | 4 | 4 |
| | 25 | 1 | 1 | 1 | 1 |
| 10 | 400 | 4 (3G) | 4 | 5 | 5 |
| | 400 | 4 | 3 | 5 (2S) | 4 |
| | 100 | 1 | 3 | 5 | 5 |
| | 100 | | | 5 | 5 |
| | 25 | 1 | 1 | 5 | 5 |
| | 25 | | | 4 | 5 |
| | 6 | | | 4 | 4 |
| 12 | 400 | 1 | 1 | 4 | 1 |
| 13 | 400 | 3 | 3 | 5 | 5 |
| | 400 | 3 | 1 (2G) | 4 | 5 |
| | 100 | 1 | 1 (2G) | 4 | 3 |
| | 25 | 1 | 1 | 1 | 1 |
| 17 | 400 | 4 | 1 | 1 | 4 |
| | 400 | 4 | | | 4 |
| | 100 | 1 | | | 1 |
| | 25 | 1 | | | 1 |
| 21 | 400 | 5 | 1 | 5 (2G) | 5 |
| | 400 | 1 (3G) | | 4 | 4 |
| | 100 | 1 | | 3 | 4 |
| | 25 | 1 | | 1 | 3 |
| 22 | 400 | 4 (3G) | 3 | 3 | 5 |
| | 400 | 3 | 3 | 3 | 4 |
| | 100 | 3 | 1 | 1 | 4 |
| | 100 | | | | 4 |
| | 25 | 1 | 1 | 1 | 4 |
| | 25 | | | | 4 |
| | 6 | | | | 1 |
| 23 | 400 | 5 | 1 (2G) | 4 (2G) | 4 |
| | 400 | 1 | | 4 | 4 |
| | 100 | 1 | | 4 | 4 |
| | 25 | 1 | | 1 | 1 |
| 24 | 400 | 4 | 1 | 1 | 1 |
| | 400 | 1 | | | |
| | 100 | 1 | | | |
| | 25 | 1 | | | |
| 25 | 400 | 4 | 1 | 5 (2G) | 1 |
| | 400 | 1 | | 4 | |
| | 100 | 1 | | 1 | |
| | 25 | 1 | | 1 | |
| 26 | 400 | 4 | 1 | 4 | 4 |
| | 400 | 3 | | 3 | 1 |
| | 100 | 1 | | 1 | 1 |
| | 25 | 1 | | 1 | 1 |
| 27 | 400 | 5 (2G) | 4 (2G) | 4 (2G) | 4 (2G) |
| | 400 | 5 | 1 | 4 | 4 (2G) |
| | 100 | 3 | 1 | 4 | 3 |
| | 25 | 1 | 1 | 1 | 1 |
| 28 | 400 | 4 | 1 | 5 | 1 |
| | 400 | 3 | | 5 | |
| | 100 | 1 | | 4 | |
| | 100 | | | 1 | |
| | 25 | 1 | | 3 | |
| | 25 | | | 1 | |
| | 6 | | | 1 | |
| 30 | 400 | 5 | 3 | 5 | 5 (2G) |
| | 400 | 4 | 1 | 5 | 4 |
| | 400 | 4 | | 5 | 5 |
| | 400 | 4 | | 5 | 5 |
| | 100 | 4 | | 5 | 5 |
| | 100 | 4 | | 5 | 5 |
| | 100 | 1 | | 4 | 4 |
| | 100 | | | 4 | |
| | 25 | 4 | | 4 | 4 |
| | 25 | 1 | | 4 | 4 |
| | 25 | 1 | | 3 | 3 |
| | 25 | | | 1 | 1 |
| | 6 | 1 | | 3 | 3 |
| | 6 | | | 1 | 1 |
| 31 | 400 | 4 | 1 | 1 | 4 |
| | 400 | 3 | | | 1 |
| | 100 | 3 | | | 1 |
| | 25 | 1 | | | 1 |
| 32 | 400 | 3 | 1 | 4 | 4 |
| | 400 | | | 4 | 4 |
| | 100 | | | 3 | 1 |
| | 25 | | | 1 | 1 |
| 33 | 400 | 4 | 3 | 5 | 5 |
| | 400 | 4 | | 5 | 5 |
| | 100 | 1 | | 5 | 4 |

TABLE 4-continued

Foliar Application

| Example No. of Compound Tested | Concentration ppm | Powdery Mildew | Leaf Rust | Helminthosporium | Septoria |
|---|---|---|---|---|---|
| | 100 | | | 5 | 4 |
| | 25 | 1 | | 4 | 3 |
| | 25 | | | 1 | 1 |
| | 6 | | | 3 | 1 |
| 34 | 400 | 1 | 1 | 1 | 3 |
| 35 | 400 | 1 | 1 | 5 (2G) | 4 |
| | 400 | | | 4 (2G) | 3 |
| | 100 | | | 4 | 3 |
| | 25 | | | 1 | 1 |
| 36 | 400 | 1 | 1 | 1 | 1 |
| 37 | 400 | 1 | 1 | 4 | 5 |
| | 400 | | | 4 | 5 |
| | 100 | | | 3 | 1 |
| | 25 | | | 1 | 1 |
| 38 | 400 | 1 | 1 | 5 | 1 |
| | 400 | | | 1 | |
| | 100 | | | 1 | |
| | 25 | | | 1 | |
| 39 | 400 | 1 | 1 | 5 (3G) | 4 (3G) |
| 40 | 400 | 1 | 4 | 5 | 5 |
| | 400 | | 4 | 5 | 5 |
| | 100 | | 3 | 4 | 3 |
| | 25 | | 1 | 1 | 1 |
| 41 | 400 | 5 | 1 | 1 | 4 (2G) |
| | 400 | 4 | | | 4 (2G) |
| | 100 | 5 | | | 1 |
| | 100 | 3 | | | |
| | 25 | 4 | | | 1 |
| | 25 | 1 | | | |
| | 6 | 1 | | | |
| 44 | 400 | 3 | 1 | 1 | 5 |
| | 400 | 1 | | | 4 |
| | 100 | 1 | | | 4 |
| | 25 | 1 | | | 1 |
| 47 | 400 | 1 | 1 | 4 | 1 |
| | 400 | | | 1 | |
| | 100 | | | 1 | |
| | 25 | | | | 1 |
| 48 | 400 | 4 | 1 | 5 | 5 |
| | 400 | 4 | | 5 | 5 |
| | 100 | 1 | | 5 (2S) | 5 |
| | 100 | | | 4 | 4 |
| | 25 | 1 | | 3 | 4 |
| | 25 | | | 1 | 1 |
| | 6 | | | 1 | 1 |
| 49 | 400 | 5 | 1 (2G) | 5 | 5 (2G) |
| | 400 | 4 | | 4 | 4 (3G) |
| | 100 | 4 | | 3 | 4 (3G) |
| | 100 | 5 | | | 5 (2G) |
| | 25 | 3 | | 1 | 4 (3G) |
| | 25 | 3 | | | 1 (2G) |
| | 6 | 1 | | | 1 |
| 50 | 400 | 3 | 1 | 1 | 1 |
| 51 | 400 | 1 | 1 | 4 | 1 (3G) |
| | 400 | | | 4 | |
| | 100 | | | 1 | |
| | 25 | | | 1 | |
| 52 | 400 | 5 (2G) | 4 | 5 | 5 |
| | 400 | 5 | 3 | 5 | 4 |
| | 100 | 5 | 1 | 5 | 5 |
| | 100 | 4 | | 5 | 5 |
| | 25 | 4 | 1 | 5 | 5 |
| | 25 | 4 | | 4 | 5 |
| | 6 | 3 | | 3 | 3 |
| 53 | 400 | 1 | 1 (2G) | 4 (2C) | 4 |
| | 400 | | | 4 (2C) | 1 (2G) |
| | 100 | | | 1 | 1 |
| | 25 | | | 1 | 1 |
| 54 | 400 | 5 | 1 | 5 | 5 |
| | 400 | 4 | | 4 | 3 |
| | 100 | 4 | | | |
| | 100 | 4 | | 1 | 1 |
| | 25 | 4 | | 1 | 1 |
| | 25 | 3 | | | |
| | 6 | 1 | | | |
| 55 | 400 | 5 (2G) | 1 | 5 | 1 |
| | 400 | 1 | | 5 | |
| | 100 | 1 | | 1 | |
| | 25 | 1 | | 1 | |
| 56 | 400 | 4 (2G) | 1 | 5 | 1 |
| | 400 | 3 | | 4 | |
| | 100 | 1 | | 1 | |
| | 25 | 1 | | 1 | |

TABLE 5

Soil Drench Application

| Example No. of Compound Tested | Concentration lbs/acre (kg/ha) | Powdery Mildew | Leaf Rust | Helminthosporium | Septoria |
|---|---|---|---|---|---|
| 1 | 11.0(12.3) | 1 | 1 | 1 | 1 |
| 2 | 11.0(12.3) | 1 | 1 | 1 | 1 |
| 3 | 11.0(12.3) | 1 | 1 | 1 | 1 |
| 4 | 11.0(12.3) | 1 | 1 | 3 | 1 |
| 5 | 11.0(12.3) | 1 | 1 | 1 | 1 |
| 6 | 11.0(12.3) | 1 | 1 | 1 | 1 |
| 7 | 11.0(12.3) | 1 | 1 | 1 | 1 |
| 8 | 11.0(12.3) | 1 | 1 | 1 | 1 |
| 9 | 11.0(12.3) | 1 | 1 | 1 | 1 |
| 10 | 11.0(12.3) | 1 | 1 | 1 | 1 |
| 12 | 11.0(12.3) | 1 | 1 | 1 | 1 |
| 13 | 11.0(12.3) | 1 | 1 | 1 | 1 |
| 17 | 11.0(12.3) | 1 | 1 | 1 | 1 |
| 21 | 11.0(12.3) | 1 | 1 | 1 | 1 |
| 22 | 11.0(12.3) | 1 | 1 | 3 (2G) | 1 |
| 23 | 11.0(12.3) | 1 | 1 | 1 | 1 |
| 24 | 11.0(12.3) | 1 | 1 | 1 | 1 |
| 25 | 11.0(12.3) | 1 | 1 | 1 | 4 |
| | 11.0(12.3) | 1 | 1 | 1 | 5 |
| | 3.0(3.36) | | | | 4 |
| | 0.7(0.78) | | | | 1 |
| 26 | 11.0(12.3) | 4 | 1 | 1 | 1 |
| | 11.0(12.3) | 1 | | | |
| | 3.0(3.36) | 1 | | | |
| | 0.7(0.78) | 1 | | | |
| 27 | 11.0(12.3) | 1 | 1 | 1 | 1 |
| 28 | 11.0(12.3) | 1 | 1 | 5 | 1 |
| | 11.0(12.3) | | | 3 | |
| | 3.0(3.36) | | | 1 | |
| | 0.7(0.78) | | | 1 | |
| 29 | 11.0(12.3) | 1 | 1 | 1 | 1 |
| 30 | 11.0(12.3) | 4 (2S) | 1 | 1 | 1 |
| | 11.0(12.3) | 4 | 1 | 1 | 1 |
| | 11.0(12.3) | 1 | | | |
| | 11.0(12.3) | 1 | | | |
| | 3.0(3.36) | 1 | | | |
| | 3.0(3.36) | 1 | | | |
| | 0.7(0.78) | 1 | | | |
| | 0.7(0.78) | 1 | | | |
| 31 | 11.0(12.3) | 1 | 1 | 1 | 1 |
| 32 | 11.0(12.3) | 1 | 1 | 1 | 1 |
| 33 | 11.0(12.3) | 4 | 1 | 1 | 1 |
| | 11.0(12.3) | 1 | | | |
| | 3.0(3.36) | 1 | | | |
| | 0.7(0.78) | 1 | | | |
| 47 | 11.0(12.3) | 1 | 1 | 1 | 1 |
| 48 | 11.0(12.3) | 1 | 1 | 1 | 1 |
| 49 | 11.0(12.3) | 1 | 1 | 1 | 1 |
| 50 | 11.0(12.3) | 1 | 1 | 1 | 1 |
| 51 | 11.0(12.3) | | 1 | 1 | 1 |
| 52 | 11.0(12.3) | 1 | 1 | 1 | 1 |
| 53 | 11.0(12.3) | 1 | 1 | 1 | 1 |
| 54 | 11.0(12.3) | 4 (2G) | 1 | 1 | 1 |
| | 11.0(12.3) | 1 | | | |
| | 3.0(3.36) | 1 | | | |
| | 0.7(0.78) | 1 | | | |
| 55 | 11.0(12.3) | 1 | 1 | 1 | 1 |
| 56 | 11.0(12.3) | 4 | 1 | 1 | 1 |
| | 11.0(12.3) | 1 | | | |
| | 3.0(3.36) | 1 | | | |

TABLE 5-continued

| Soil Drench Application | | | | |
|---|---|---|---|---|
| Example No. of Compound Tested | Concentration lbs/acre (kg/ha) | Powdery Mildew | Leaf Rust | Helminthosporium | Septoria |
| | 0.7(0.78) | 1 | | | |

EXPERIMENT 4

Certain compounds of this invention have additionally been evaluated in soil disease tests to demonstrate their antifungal activity. Test compounds were formulated by dissolving 57 mg of compound in 1 ml of a fifty percent (v/v) solution of acetone and ethanol. A 0.1% aqueous solution of Tween 20 was added to bring the final volume to 16 ml.

Pathogen-infested soil was placed in 8 oz paper cups. A depression was made in the surface of the soil and 3 g of Celatom MP-78 granules were placed in the depression. A 4 ml aliquot of chemical formulation, equivalent to a rate of 40 lbs/acre (44.8 kg/ha) or less, was added to the granules, and the cups were then covered with lids. The containers were shaken by hand for about 10 seconds, and then placed on a roller for about 10 minutes to thoroughly incorporate the test chemical into the soil. The treated soil was transferred to a 2.5 inch round plastic pot, and seeds of the host plant were added, and covered with additional treated soil. The pathogens and their host plants were as follows:

| | |
|---|---|
| Rhizoctonia | Cotton |
| Pythium | Cotton |
| Fusarium | Bean |
| Verticillium | Cotton |

The effect of the test compounds was observed on the growing plants and was rated on a scale of 1 to 5 (1 is severe disease, 5 is no disease). The results of such evaluations are presented in Table 6.

TABLE 6

| | | Soil Disease | | | |
|---|---|---|---|---|---|
| Example No. of Compound Tested | Concentration lbs/acre (kg/ha) | Rhizoctonia | Pythium | Fusarium | Verticillium |
| 25 | 40.0(44.8) | 3 | 1 | 3 | 1 |
| 26 | 40.0(44.8) | 4 | 1 | 4 (3S) | 1 |
| | 40.0(44.8) | 4 | | | |
| | 20.0(22.4) | 4 | | | |
| | 10.0(11.2) | 4 | | | |
| | 5.0(5.6) | 4 | | | |
| | 2.5(2.8) | 1 | | | |
| 27 | 40.0(44.8) | 5 | 1 | 4 (3S) | 1 |
| | 40.0(44.8) | 5 | | | |
| | 20.0(22.4) | 5 | | | |
| | 10.0(11.2) | 5 | | | |
| | 5.0(5.6) | 4 | | | |
| | 2.5(2.8) | 4 | | | |
| 29 | 40.0(44.8) | 1 | 1 | 1 | 1 |
| 36 | 40.0(44.8) | 5 | 1 | 4 | 1 |
| | 40.4(44.8) | 4 | | 4 | |
| | 20.0(22.4) | 5 | | 1 | |
| | 10.0(11.2) | 1 | | 1 | |
| 40 | 40.0(44.8) | 1 | 1 | 4 | 1 |
| | 40.0(44.8) | | | 4 | |
| | 20.0(22.4) | | | 4 | |
| | 10.0(11.2) | | | 1 | |
| 54 | 40.0(44.8) | 3 | 1 | 1 | 1 |
| 55 | 40.0(44.8) | 3 | 1 | 1 (3S) | 5 (2C) |
| | 40.0(44.8) | | | | 1 (2C) |

TABLE 6-continued

| | | Soil Disease | | | |
|---|---|---|---|---|---|
| Example No. of Compound Tested | Concentration lbs/acre (kg/ha) | Rhizoctonia | Pythium | Fusarium | Verticillium |
| | 20.0(22.4) | | | | 1 |
| | 10.0(11.2) | | | | 1 |

EXPERIMENT 5

Compounds of example number 7 and 30 were field tested in an effort to evaluate the compounds' ability to control certain fungal diseases. The compounds were formulated for application with a 1:1 mixture of acetone:ethanol as the solvent and Tween 20 as the surfactant. The formulated compound was diluted with water to provide the appropriate concentration of compound. The diluted formulation was applied at 31, 15 and 2 days prior to recording for the Cercospora Leaf Spot test and 43, 29 and 14 days prior to evaluation for the powdery mildew test. The results of this test appears in Table 7 below as percent inhibition.

TABLE 7

| | | Percent Control | |
|---|---|---|---|
| Example No. of Compound Tested | Application Rate ppm | Zinnia Powdery Mildew | Sugar Beet Cercospora Leaf Spot |
| 7 | 1000.0 | | 40 |
| | 500.0 | | 6 |
| | 100.0 | | 6 |
| | 50.0 | 63 | |
| | 25.0 | 63 | |
| | 12.5 | 55 | |
| 30 | 1000.0 | | 70 |
| | 500.0 | | 40 |
| | 100.0 | 83 | 0 |
| | 50.0 | 71 | |
| | 25.0 | 52 | |
| | Control | 0 | 0 |

EXPERIMENT 6

A number of compounds of the present invention were also tested in the greenhouse to evaluate their ability to control fungal diseases that commonly infest turfgrasses.

The compound was dissolved in a solution containing 1000 ppm. each of the surfactants Toximul R and S combined with a mixture of ethanol and acetone in a 1:1 ratio. This solution was then serially diluted with water to provide sprayable formulations for application rates of 0.5, 1, 2 and 4 pounds of active ingredient per acre (0.56, 1.12, 2.24 and 4.48 kg./ha. respectively). Additional dilution with water provided lower test compound concentrations. Each formulated test compound was tested against four different fungal diseases. Each compound was foliar applied to Penncross creeping bentgrass (*Agrostis palustris*) which was then artificially inoculated with Rhizoctonia spawn (*Rhizoctonia solani*), Fusarium spawn (*Fusarium roseum*), and dollarspot spawn (*Sclerotinia homoeocarpa*) in separate pots. The formulated compound was also foliar applied to common Kentucky bluegrass (*Poa pratensis*) prior to the grass being artificially inoculated with a spore suspension of Helminthosporium spp. Pennfine perennial ryegrass (*Lolium perenne*) was treated with a test compound prior to being inoculated with *Pythium aphanidermatum*. All of the individually treated, inoculated turf pots were incubated at 27° C. in a climate having greater than 90% relative humidity. The treatments were then visually evaluated 7 and 14 days following treatment for disease severity and turfgrass tolerance according to the following scales:

| Disease Severity | Turfgrass Tolerance |
|---|---|
| 5 = no disease | 1 = no injury |
| 4 = slight disease | 2 = slight injury |
| 3 = moderate disease | 3 = moderate injury |

-continued

| Disease Severity | Turfgrass Tolerance |
|---|---|
| 2 = severe disease | 4 = severe injury |
| 1 = 100% of plant tissue is infected | 5 = death of turf |

The results of this experiment appear below in Table 8. The numbers in parentheses refer to turfgrass tolerance ratings and where no value is recorded, there was no injury observed.

TABLE 8

| Example No. of Compound Tested | Application Rate lbs/acre | (kg/ha) | 7 Days Helminthosporium | Pythium | Rhizoctonia | Sclerotinia | 14 Days Helminthosporium | Pythium | Rhizoctonia | Sclerotinia |
|---|---|---|---|---|---|---|---|---|---|---|
| 1 | 4.0 | (4.48) | 5 | 1 | 5 | 4 | 5 | 2 | 5 | 4 |
|  | 2.0 | (2.24) | 5 | 1 | 5 | 3 | 5 | 2 | 5 | 3 |
|  | 1.0 | (1.12) | 5 | 1 | 5 | 2 | 4 | 1 | 5 | 2 |
|  | 0.5 | (0.56) | 3 | 1 | 4 | 2 | 3 | 1 | 5 | 3 |
| 2 | 4.0 | (4.48) | 5 | 2 | 5 | 5 | 5 | 3 | 5 | 5 |
|  | 2.0 | (2.24) | 5 | 1 | 5 | 4 | 5 | 2 | 5 | 5 |
|  | 1.0 | (1.12) | 3 | 1 | 4 | 3 | 4 | 1 | 4 | 4 |
|  | 0.5 | (0.56) | 1 | 1 | 3 | 2 | 2 | 1 | 4 | 3 |
| 4 | 4.0 | (4.48) | 3 | 4 | 4 |  | 3 | 3 | 3(2) |  |
|  | 2.0 | (2.24) | 3 | 3 | 3 |  | 2 | 1 | 1 |  |
|  | 1.0 | (1.12) | 1 | 1 | 3 |  | 1 | 1 | 1 |  |
|  | 0.5 | (0.56) | 1 | 1 | 1 |  | 1 | 1 | 1 |  |
| 6 | 4.0 | (4.48) | 3.5 | 3 | 3.5 | 5 | 3 | 2 | 3 | 5 |
|  | 2.0 | (2.24) | 3 | 3 | 3 | 5 | 3 | 1 | 2 | 5 |
|  | 1.0 | (1.12) | 3 | 1 | 3 | 5 | 1 | 1 | 2 | 5 |
|  | 0.5 | (0.56) | 2 | 1 | 2 | 4 | 1 | 1 | 2 | 4 |
| 7 | 4.0 | (4.48) | 5 | 3 | 5 | 5 | 4 | 3 | 5 | 5 |
|  | 2.0 | (2.24) | 4.5 | 3 | 5 | 5 | 3.5 | 2 | 5 | 5 |
|  | 1.0 | (1.12) | 4 | 1 | 5 | 5 | 3 | 1 | 5 | 5 |
|  | 0.5 | (0.56) | 3 | 1 | 4.5 | 4 | 1 | 1 | 4 | 4 |
| 8 | 4.0 | (4.48) | 5 | 1 | 3(2) | 5 | 4 | 1 | 3 | 5 |
|  | 2.0 | (2.24) | 5 | 1 | 3 | 5 | 3 | 1 | 2 | 5 |
|  | 1.0 | (1.12) | 4 | 1 | 3 | 5 | 3 | 1 | 3 | 5 |
|  | 0.5 | (0.56) | 2 | 1 | 1 | 5 | 1 | 1 | 1 | 5 |
| 9 | 4.0 | (4.48) | 4.5 | 3 | 5 | 5 | 4 | 3 | 5 | 5 |
|  | 2.0 | (2.24) | 4 | 1 | 5 | 5 | 3.5 | 1 | 5 | 5 |
|  | 1.0 | (1.12) | 3 | 1 | 5 | 5 | 2 | 1 | 4 | 5 |
|  | 0.5 | (0.56) | 2 | 1 | 4 | 5 | 2 | 1 | 4 | 5 |
|  | 1.0 | (1.12) |  |  |  | 4 |  |  |  | 5 |
|  | 0.5 | (0.56) |  |  |  | 4 |  |  |  | 4 |
|  | 0.25 | (0.28) |  |  |  | 4 |  |  |  | 4 |
|  | 0.125 | (0.14) |  |  |  | 4 |  |  |  | 4 |
| 10 | 4.0 | (4.48) | 3 | 3 | 4.5 | 5 | 3 | 3 | 5 | 5 |
|  | 2.0 | (2.24) | 3 | 2 | 4 | 4 | 2 | 2 | 5 | 4 |
|  | 1.0 | (1.12) | 2 | 1 | 4.5 | 4 | 1 | 2 | 4 | 4 |
|  | 0.5 | (0.56) | 1 | 1 | 4 | 4 | 1 | 2 | 4 | 4 |
| 11 | 4.0 | (4.48) | 4 | 3 | 5 | 5 | 3 | 1 | 5 | 5 |
|  | 2.0 | (2.24) | 3.5 | 1 | 5 | 5 | 2 | 1 | 5 | 5 |
|  | 1.0 | (1.12) | 3 | 1 | 4 | 5 | 1 | 1 | 5 | 5 |
|  | 0.5 | (0.56) | 1 | 1 | 4 | 5 | 1 | 1 | 5 | 5 |
|  | 1.0 | (1.12) |  |  |  | 5 |  |  |  | 5 |
|  | 0.5 | (0.56) |  |  |  | 5 |  |  |  | 4 |
|  | 0.25 | (0.28) |  |  |  | 5 |  |  |  | 4 |
|  | 0.125 | (0.14) |  |  |  | 4 |  |  |  | 4 |
| 12 | 4.0 | (4.48) | 5 | 1 | 5 | 5 | 3 | 1 | 2 | 5 |
|  | 2.0 | (2.24) | 5 | 1 | 5 | 5 | 5 | 1 | 4 | 5 |
|  | 1.0 | (1.12) | 4 | 1 | 4 | 5 | 4 | 1 | 4 | 5 |
|  | 0.5 | (0.56) | 3 | 1 | 3 | 5 | 3 | 1 | 2 | 5 |
| 15 | 4.0 | (4.48) | 5 | 2(2) | 5(2) | 5 | 4.5 | 2 | 5 | 5 |
|  | 2.0 | (2.24) | 4 | 1 | 5 | 5 | 4 | 1 | 5 | 5 |
|  | 1.0 | (1.12) | 4 | 1 | 4 | 4 | 3 | 1 | 5 | 4 |
|  | 0.5 | (0.56) | 4 | 1 | 4 | 4 | 2 | 1 | 4.5 | 4 |
| 23 | 4.0 | (4.48) |  |  |  |  | 3 | 3 | 3(2) | 5(2) |
|  | 2.0 | (2.24) |  |  |  |  | 2 | 2 | 4 | 5 |
|  | 1.0 | (1.12) |  |  |  |  | 2 | 2 | 3 | 4 |
|  | 0.5 | (0.56) |  |  |  |  | 1 | 2 | 3 | 4 |
| 24 | 4.0 | (4.48) |  |  |  |  | 3(2) | 3 | 3 | 4 |
|  | 2.0 | (2.24) |  |  |  |  | 2 | 3 | 1 | 3 |
|  | 1.0 | (1.12) |  |  |  |  | 1 | 2 | 1 | 4 |
|  | 0.5 | (0.56) |  |  |  |  | 1 | 3 | 1 | 3 |
| 25 | 4.0 | (4.48) |  |  |  |  | 2 | 3 | 4(3) | 5(2) |
|  | 2.0 | (2.24) |  |  |  |  | 1 | 3 | 4 | 5 |
|  | 1.0 | (1.12) |  |  |  |  | 1 | 3 | 3 | 5 |
|  | 0.5 | (0.56) |  |  |  |  | 1 | 3 | 3 | 5 |

TABLE 8-continued

| Example No. of Compound Tested | Application Rate lbs/acre (kg/ha) | | 7 Days | | | | 14 Days | | | |
|---|---|---|---|---|---|---|---|---|---|---|
| | | | Helmintho-sporium | Pythium | Rhizoc-tonia | Sclero-tinia | Helmintho-sporium | Pythium | Rhizoc-tonia | Sclero-tinia |
| 26 | 4.0 | (4.48) | 4 | 1 | (4) | 5 | 4 | 1 | (4) | (4) |
| | 2.0 | (2.24) | 4 | 1 | 3 | 5 | 4 | 1 | 3 | 5 |
| | 1.0 | (1.12) | 2 | 1 | 3 | 5,4 | 2 | 1 | 3 | 5,4 |
| | 0.5 | (0.56) | 1 | 1 | 4 | 5,4 | 1 | 1 | 4 | 5,4 |
| | 0.25 | (0.28) | | | | 3 | | | | 3 |
| | 0.125 | (0.14) | | | | 3 | | | | 2 |
| 27 | 4.0 | (4.48) | 5 | 1 | 5(4) | 5(4) | 5(3) | 1 | 4(4) | 5(2) |
| | 2.0 | (2.24) | 5 | 1 | 4(3) | 5(3) | 5(2) | 1 | 4(3) | 5 |
| | 1.0 | (1.12) | 5 | 1 | 4(2) | 5,5 | 5 | 1 | 4(2) | 5,5 |
| | 0.5 | (0.56) | 3 | 1 | 4 | 5,5 | 3 | 1 | 4 | 5,5 |
| | 0.25 | (0.28) | | | | 5 | | | | 5 |
| | 0.125 | (0.14) | | | | 4 | | | | 4 |
| 28 | 1.0 | (1.12) | | | 5 | | | | 5 | |
| | 0.5 | (0.56) | | | 5 | | | | 5 | |
| | 0.25 | (0.28) | | | 5 | | | | 5 | |
| | 0.125 | (0.14) | | | 4 | | | | 4 | |
| 30 | 4.0 | (4.48) | | 1 | 4 | 5 | | 1 | 4(2) | 5 |
| | 2.0 | (2.24) | | 1 | 4 | 5 | | 1 | 4 | 5 |
| | 1.0 | (1.12) | 5 | 1 | 3,5 | 5,5 | 5 | 1 | 4,5 | 5,5 |
| | 0.5 | (0.56) | 5 | 1 | 3,5 | 5,5 | 5 | 1 | 4,5 | 5,5 |
| | 0.25 | (0.28) | 5 | | 4 | 5 | 5 | | 5 | 5 |
| | 0.125 | (0.14) | 5,5 | | 4,5 | 5,5 | 5,4 | | 4,4 | 5,5 |
| | 0.0625 | (0.07) | 4 | | 5 | 4 | 3 | | 4 | 4 |
| | 0.031 | (0.04) | 3 | | 4 | 4 | 2 | | 4 | 4 |
| | 0.016 | (0.02) | 2 | | 3 | 4 | 1 | | 3 | 4 |
| 31 | 4.0 | (4.48) | | 1 | 1 | 1 | | 1 | 1 | 1 |
| | 2.0 | (2.24) | | 1 | 1 | 1 | | 1 | 1 | 1 |
| | 1.0 | (1.12) | | 1 | 1 | 1 | | 1 | 1 | 1 |
| | 0.5 | (0.56) | | 1 | 1 | 1 | | 1 | 1 | 1 |
| 32 | 4.0 | (4.48) | | 1 | 4 | 5 | | 1 | 5 | 5 |
| | 2.0 | (2.24) | | 1 | 4 | 4 | | 1 | 5 | 5 |
| | 1.0 | (1.12) | | 1 | 3 | 4 | | 1 | 4 | 5 |
| | 0.5 | (0.56) | | 1 | 3 | 3 | | 1 | 4 | 4 |
| 34 | 4.0 | (4.48) | | | | | 5 | 4 | 5(3) | 5(2) |
| | 2.0 | (2.24) | | | | | 5 | 1 | 5 | 5 |
| | 1.0 | (1.12) | 5 | | 4 | 5 | 5,5 | 1 | 4,4 | 5,5 |
| | 0.5 | (0.56) | 5 | | 3 | 5 | 4,5 | | 3,3 | 4,4 |
| | 0.25 | (0.28) | 5 | | 1 | 4 | 5 | | 2 | 4 |
| | 0.125 | (0.14) | 3 | | 1 | 4 | 5 | | 1 | 4 |
| 35 | 4.0 | (4.48) | | | | | 5 | 3 | 5(2) | 5 |
| | 2.0 | (2.24) | | | | | 5 | 1 | 5 | 5 |
| | 1.0 | (1.12) | 5 | | 4 | 5 | 4,5 | 1 | 5,4 | 5,5 |
| | 0.5 | (0.56) | 5 | | 4 | 5 | 4,5 | 1 | 4,4 | 5,5 |
| | 0.25 | (0.28) | 4 | | 3 | 4 | 4 | | 3 | 5 |
| | 0.125 | (0.14) | 3 | | 2 | 4 | 4 | | 2 | 4 |
| 36 | 4.0 | (4.48) | | | | | 5 | 1 | 4(2) | 5(2) |
| | 2.0 | (2.24) | | | | | 5 | 1 | 4 | 5(2) |
| | 1.0 | (1.12) | 5 | | 3 | 5 | 4,4 | 1 | 3,4 | 5,5 |
| | 0.5 | (0.56) | 4 | | 4 | 5 | 4,4 | 1 | 3,4 | 4,5 |
| | 0.25 | (0.28) | 3 | | 3 | 5 | 3 | | 3 | 4 |
| | 0.125 | (0.14) | 2 | | 1 | 5 | 3 | | 2 | 4 |
| 37 | 4.0 | (4.48) | | | | | 5 | 1 | 5(2) | 5(2) |
| | 2.0 | (2.24) | | | | | 5 | 1 | 5 | 5(2) |
| | 1.0 | (1.12) | 5 | | 5 | 5 | 5,5 | 1 | 5,5 | 5(2),5 |
| | 0.5 | (0.56) | 5 | | 5 | 5 | 5,5 | 1 | 5,5 | 5,5 |
| | 0.25 | (0.28) | 5 | | 5 | 5 | 4 | | 4 | 4 |
| | 0.125 | (0.14) | 4,3 | | 4,4 | 4,5 | 3,4 | | 4,4 | 4,5 |
| | 0.06 | (0.07) | 2 | | 4 | 4 | 1 | | 4 | 3 |
| | 0.03 | (0.04) | 1 | | 4 | 4 | 1 | | 4 | 3 |
| | 0.02 | (0.02) | 1 | | 3 | 3 | 1 | | 4 | 3 |
| 39 | 4.0 | (4.48) | | | | | 5 | 1 | 5(2) | 5(2) |
| | 2.0 | (2.24) | | | | | 5 | 1 | 4 | 5 |
| | 1.0 | (1.12) | 5 | | 4 | 5 | 5,5 | 1 | 4,4 | 5,5 |
| | 0.5 | (0.56) | 5 | | 4 | 5 | 4,5 | 1 | 4,4 | 5,5 |
| | 0.25 | (0.28) | 4 | | 3 | 4 | 4 | | 3 | 4 |
| | 0.125 | (0.14) | 3 | | 2 | 4 | 3 | | 2 | 4 |
| 40 | 4.0 | (4.48) | | | | | 5 | 1 | 5(4) | 5(3) |
| | 2.0 | (2.24) | | | | | 5 | 1 | 5 | 5(2) |
| | 1.0 | (1.12) | 5 | | 5 | 5 | 5,5 | 1 | 5,5 | 4(2),5 |
| | 0.5 | (0.56) | 5 | | 5 | 5 | 5,5 | 1 | 5,5 | 4(2),5 |
| | 0.25 | (0.28) | 5 | | 5 | 5 | 4 | | 5 | 5 |
| | 0.125 | (0.14) | 4 | | 4 | 5 | 4 | | 5 | 5 |
| 41 | 4.0 | (4.48) | | | | | 4(2) | 1 | 4(2) | 5(3) |
| | 2.0 | (2.24) | | | | | 4(2) | 1 | 3 | 5(2) |
| | 1.0 | (1.12) | | | 5 | | 3 | 1 | 3 | 5,5 |
| | 0.5 | (0.56) | | | 5 | | 2 | | | 5,5 |
| | 0.25 | (0.28) | | | 5 | | | | | 4 |
| | 0.125 | (0.14) | | | 4 | | | | | 4 |

TABLE 8-continued

| Example No. of Compound Tested | Application Rate lbs/acre (kg/ha) | | 7 Days | | | | 14 Days | | |
|---|---|---|---|---|---|---|---|---|---|
| | | Helmintho-sporium | Pythium | Rhizoc-tonia | Sclero-tinia | Helmintho-sporium | Pythium | Rhizoc-tonia | Sclero-tinia |
| 42 | 4.0 (4.48) | | | | | 4 | 4 | 4(2) | 5(2) |
| | 2.0 (2.24) | | | | | 4 | 1 | 4 | 5 |
| | 1.0 (1.12) | | | 4 | 5 | 3 | 1 | 4,4 | 5,5 |
| | 0.5 (0.56) | | | 4 | 5 | 3 | 1 | 4,4 | 4,5 |
| | 0.25 (0.28) | | | 3 | 4 | | | 3 | 4 |
| | 0.125 (0.14) | | | 2 | 4 | | | 2 | 4 |
| 43 | 4.0 (4.48) | | | | | 5 | 1 | 5(2) | 5(2) |
| | 2.0 (2.24) | | | | | 5 | 1 | 5 | 5 |
| | 1.0 (1.12) | 5 | | 5 | 5 | 5,5 | 1 | 5,5 | 5,5 |
| | 0.5 (0.56) | 5 | | 5 | 5 | 5,5 | 1 | 4,5 | 5,5 |
| | 0.25 (0.28) | 5 | | 5 | 5 | 5 | | 5 | 5 |
| | 0.125 (0.14) | 4 | | 4 | 4 | 5 | | 4 | 4 |
| 45 | 4.0 (4.48) | 5 | 1 | 5(2) | 5(2) | 5 | 1 | 5 | 5 |
| | 2.0 (2.24) | 5 | 1 | 5(2) | 5(2) | 5 | 1 | 5 | 5 |
| | 1.0 (1.12) | 5 | 1 | 4 | 5 | 5 | 1 | 5 | 5 |
| | 0.5 (0.56) | 4 | 1 | 3 | 4 | 4 | 1 | 4 | 4 |
| 46 | 4.0 (4.48) | 5 | 1 | 5(2) | 5 | 5 | 1 | 5 | 5 |
| | 2.0 (2.24) | 5 | 1 | 5(2) | 5 | 5 | 1 | 5 | 5 |
| | 1.0 (1.12) | 5,5 | 1 | 5,5 | 5,4 | 5,5 | 1 | 5,5 | 5,4 |
| | 0.5 (0.56) | 5,4 | 1 | 5,5 | 5,4 | 5,4 | 1 | 5,5 | 5,5 |
| | 0.25 (0.28) | 3 | | 4 | 5 | 3 | | 4 | 4 |
| | 0.125 (0.14) | 3 | | 4 | 4 | 3 | | 4 | 4 |
| 47 | 4.0 (4.48) | 2 | 2 | 5 | 4 | 3 | 3 | 5 | 4 |
| | 2.0 (2.24) | 1 | 1 | 5 | 3 | 2 | 1 | 5 | 4 |
| | 1.0 (1.12) | 1 | 1 | 5 | 2 | 2 | 1 | 5 | 3 |
| | 0.5 (0.56) | 1 | 1 | 3 | 2 | 2 | 1 | 4 | 3 |
| 48 | 4.0 (4.48) | 5 | 2 | 5 | 5(3) | 5 | 2 | 5 | 5 |
| | 2.0 (2.24) | 5 | 1 | 5 | 5(2) | 5 | 1 | 5 | 5 |
| | 1.0 (1.12) | 5,5 | 1 | 4,5 | 5,5 | 5,4 | 1 | 5,5 | 5 |
| | 0.5 (0.56) | 5,5 | 1 | 4,5 | 5,4 | 5,3 | 1 | 5,5 | 5,5 |
| | 0.25 (0.28) | 4 | | 4 | 4 | 3 | | 4 | 4 |
| | 0.125 (0.14) | 3 | | 3 | 4 | 2 | | 3 | 4 |
| 49 | 4.0 (4.48) | 5 | 1 | 5 | 5 | 5 | 1 | 5 | 5 |
| | 2.0 (2.24) | 4 | 1 | 5 | 4 | 5 | 1 | 5 | 5 |
| | 1.0 (1.12) | 4 | 1 | 4 | 4 | 4 | 1 | 4 | 5 |
| | 0.5 (0.56) | 3 | 1 | 3 | 3 | 3 | 1 | 4 | 4 |
| 50 | 4.0 (4.48) | 4 | 2 | 5 | 4 | 4 | 2 | 5 | 5 |
| | 2.0 (2.24) | 3 | 1 | 4 | 4 | 2 | 1 | 4 | 5 |
| | 1.0 (1.12) | 1 | 1 | 4 | 4 | 1 | 1 | 4 | 4 |
| | 0.5 (0.56) | 1 | 1 | 4 | 3 | 1 | 1 | 4 | 4 |
| 51 | 4.0 (4.48) | 5 | 1 | 5(2) | 5(2) | 5 | 1 | 4(3) | 5 |
| | 2.0 (2.24) | 5 | 1 | 4(2) | 4 | 4 | 1 | 4 | 5 |
| | 1.0 (1.12) | 4 | 1 | 3 | 4 | 4 | 1 | 3 | 5 |
| | 0.5 (0.56) | 1 | 1 | 3 | 4 | 1 | 1 | 3 | 5 |
| 52 | 4.0 (4.48) | 5 | 1 | 5 | 5 | 5 | 1 | 5 | 5 |
| | 2.0 (2.24) | 5 | 1 | 5 | 5 | 5 | 1 | 5 | 5 |
| | 1.0 (1.12) | 5,5 | 1 | 5,5 | 5,5 | 5,5 | 1 | 5,5 | 5,5 |
| | 0.5 (0.56) | 5,5 | 1 | 5,5 | 5,5 | 5,5 | 1 | 5,5 | 5,5 |
| | 0.25 (0.28) | 5 | | 5 | 5 | 4 | | 5 | 5 |
| | 0.125 (0.14) | 4 | | 5 | 5 | 3 | | 5 | 5 |
| 54 | 4.0 (4.48) | 5 | 1 | 5 | 5 | 5 | 1 | 5 | 5 |
| | 2.0 (2.24) | 5 | 1 | 5 | 5 | 5 | 1 | 5 | 5 |
| | 1.0 (1.12) | 5 | 1 | 5 | 5 | 5 | 1 | 5. | 4 |
| | 0.5 (0.56) | 4 | 1 | 5 | 5 | 4 | 1 | 5 | 5 |

EXPERIMENT 7

Compounds of example number 30 and 37 were tested in a field study in an effort to evaluate the ability of the compounds to control the growth of the fungal disease helminthosporium leaf spot on turfgrass. The compounds were formulated by dissolving them in a 1:1 mixture of acetone:methanol containing the surfactants Toximul R and S. The formulated compounds were then diluted with water to provide the corresponding application rate. The diluted formulation was applied to helminthorporium infested Kentucky bluegrass. The treatments were visually evaluated and compared to control plots for disease severity at both 33 and 40 days after application. Table 9 gives the percent disease control as the average of three replications.

TABLE 9
Turfgrass Field Study

| Example No. of Compound Tested | Application Rate lbs/acre (kg/ha) | Percent Disease Control of Helminthosporium Days After Application | |
|---|---|---|---|
| | | 33 | 46 |
| 30 | 4.0(4.48) | 83.9 | 100.0 |
| | 2.0(2.24) | 78.6 | 76.9 |
| | 1.0(1.12) | 73.2 | 76.9 |
| | 0.5(0.56) | 57.1 | 59.6 |
| 37 | 4.0(4.48) | 73.2 | 65.4 |
| | 2.0(2.24) | 83.9 | 82.7 |
| | 1.0(1.12) | 57.1 | 88.5 |
| | 0.5(0.56) | 19.6 | 42.3 |
| Control | | 0 | 0 |

The compounds of the present invention may be formulated with a suitable agriculturally-acceptable carrier to provide yet another embodiment of the invention. Such compositions will contain from about 0.1 to about 95.0 percent by weight of the active ingredient, depending on the composition desired. Preferred formulations will contain from about 1 to about 50 percent active ingredient. Sprayable formulations are preferred primarily because of their rapidity and economy of application.

The most convenient formulations contemplated are in the form of concentrated compositions. Such formulations are diluted with water, generally at or near the site of application and are applied by spraying the resulting water dispersion or emulsion. The diluted compositions generally will contain the active ingredient in the range from about 0.1 percent to about 10 percent by weight. Water-dispersible or emulsifiable compositions may be either solids, usually known as wettable powders, or liquids, usually known as emulsifiable concentrates or aqueous suspensions.

A typical wettable powder comprises an intimate mixture of a compound of the invention, an inert carrier, and one or more surfactants. The concentration of the active compound is usually from about 5 percent to about 90 percent by weight, ideally about 25 to about 80 percent. The inert carrier is usually chosen from among the attapulgite clays, the montmorillonite clays, the diatomaceous earths, the purified silicates, or other similar substances that are readily available. Effective surfactants, comprising from about 0.5 percent to about 15 percent by weight of the wettable powder, are chosen from among the sulfonated lignins, the condensed naphthalenesulfonates, the alkyl sulfates, and related materials.

The most popular type of formulation is an emulsifiable concentrate. A typical emulsifiable concentrate comprises from about 0.1 to about 6 pounds of a compound of the invention per gallon of liquid (0.012 to 0.72 kg/l.), dissolved in a mixture of an organic solvent and an emulsifier. The organic solvent will be immiscible with water and is chosen with regard to its solvency and its cost. Examples of solvents which may be employed include the aromatics, especially the xylenes, 2-chlorotoluene, acetophenone, isophorone and heavy aromatic naphtha. Hydrophilic cosolvents such as cyclohexanone and the glycol ethers such as 2-methoxyethanol may be included. Other organic solvents may also be used, including the terpenic solvents and kerosene. Suitable emulsifiers for emulsifiable concentrates are chosen from the alkylbenzenesulfonates, naphthalenesulfonates, and nonionic surfactants such as ethoxylated alkyl phenols, ethoxylated alkyl ethers, sorbitan esters, ethoxylated alkyl alcohols, and ethoxylated sorbitan esters and ethers, and are used at similar percentages as for wettable powders.

Dust compositions are most often prepared for fungicides and will typically contain a lower level of the active ingredient than will be present in other formulations and will be dispersed in finely divided inert carriers. Dusts generally will contain a compound of the present invention in an amount from about 0.1 to about 10 percent by weight. Dusts are prepared by intimately mixing and finely grinding the compound with an inert solid diluent or carrier such as ground montmorillonite clay, attapulgite clay, talc, ground volcanic rock, kaolin clay, or other inert, relatively dense, inexpensive substances.

Solid, granular compositions are convenient for the application of compounds of this invention to the soil. Granules comprise a compound of the invention dispersed on a granular inert carrier such as coarsely ground clay of from about 0.1 to about 3 mm particle size. The compound is most conveniently applied to the clay by dissolving it in an inexpensive solvent such as acetone and applying the solution to the sized clay in an appropriate solids mixer. The solvent is then removed by evaporation or the like.

The following examples provide an illustration of typical agricultural compositions comprehended by this invention.

| Wettable Powder | |
|---|---|
| Ingredient | Concentration by weight (%) |
| (N—Butyl-N—(2,4-dichlorophenyl)-[(3-pyridyl)methyl]amine | 45.0 |
| Igepal CA6.30, a polyoxyethylene octyl phenol nonionic wetting agent-GAF Corp. | 10.0 |
| Polyfon O, emulsifier from Westvaco Corp. | 5.0 |
| Zeolex 7, a hydrated silicate from J.M. Huber Corp. | 5.0 |
| Barden Clay from J.M. Huber Corp. | 35.0 |
| | 100.0 |

The active ingredient is finely divided into a powder and blended to uniformity with the agronomic carriers using a hammer mill or micro mill to form a free flowing powder that will be wetted and suspendible in water at or near the site of application to form a sprayable mixture. The composition is then sprayed on the locus where control is desired. The application is done at a volume rate so that the active ingredient is present at about 1 to about 4 pounds per acre (about 1.12 to about 4.48 kg/ha).

| Dust | |
|---|---|
| Ingredient | Concentration by weight (%) |
| N—(Cyclopropylmethyl)-N—(2,4-dichlorophenyl-[(3-pyridyl)methyl]amine | 5.0 |
| Diatomite, a diatomaceous earth, Witco Chemical Corp., Inorganic Specialities Division | 95.0 |
| | 100.0 |

The active ingredient is suspended in a solvent such as acetone and sprayed onto a carrier such as diatomaceous earth. The solvent is then removed by evaporation and the dry mixture is ground to a fine powder of uniform particle size of about 10 to about 40 microns. The dust formulation can be diluted at the site of application if desired by the addition of additional excipient such as silica or clay. The dust is surface applied to the locus where control is desired, either by conventional ground equipment or aerially.

| Granules | |
|---|---|
| Ingredient | Concentration by weight (%) |
| N—(2,4-Dichlorophenyl)-N—[(4-chlorophenyl)methyl]-[(3-pyridyl)methyl]amine | 5.0 |
| Heavy aromatic naphtha | 5.0 |
| Florex 30/60 granular clay, The Floridin Company | 90.0 |

-continued

| Granules | |
|---|---|
| Ingredient | Concentration by weight (%) |
| | 100.0 |

The active agent is dissolved in the naphtha and sprayed onto the clay granules, typically under agitation, and the formulated granules are sieved to provide a uniform mesh size.

| Aqueous Suspension | |
|---|---|
| Ingredient | Concentration by weight (%) |
| N—Methyl-N—(4-chlorophenyl)-[1-(3-pyridyl)-ethyl]amine | 45.0 |
| Polyfon H, emulsifier from Westvaco Corporation | 3.0 |
| Sponto 2174, emulsifier from Witco Chemical Corporation | 4.0 |
| Ethylene Glycol | 8.0 |
| Xanthum Gum thickening agent | 0.2 |
| Antifoam C foam suppressant, from Dow Corning | 0.5 |
| Water | 39.3 |
| | 100.0 |

Typically the water and soluble components are mixed in a tank equipped with a high shear mixer. The solid active ingredient is next added and mixed. The entire mixture is then passed through a liquid grinding mill until the desired particle size is reached. The final step in the preparation of the suspension is to blend the xanthum gum to the mixture. The aqueous suspension is then typically diluted with additional water and sprayed on the application site.

We claim:

1. A method for controlling the growth of fungal diseases which comprises applying to the locus of the plant for which control is desired a disease inhibiting and non-herbicidal amount of a compound of the formula

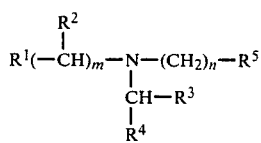

wherein:

R$^1$ is 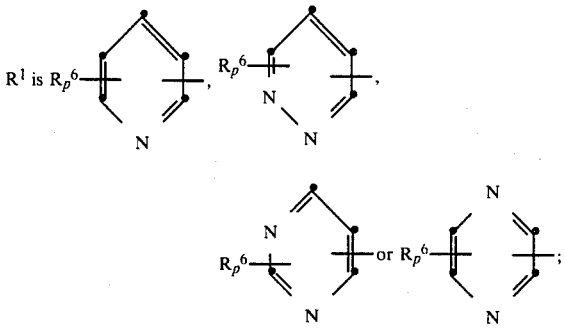

R$^2$ is hydrogen, C$_1$–C$_6$ alkyl, phenyl or phenyl mono-substituted with C$_1$–C$_4$ alkyl, C$_1$–C$_4$ alkoxy, halogen C$_1$–C$_4$ haloalkyl or C$_1$–C$_4$ haloalkoxy;

R$^3$ is hydrogen or phenyl;
R$^4$ is hydrogen, C$_1$–C$_{12}$ alkyl, C$_1$–C$_{10}$ haloalkyl, C$_2$–C$_{10}$ alkenyl, C$_2$–C$_{10}$ alkynyl,

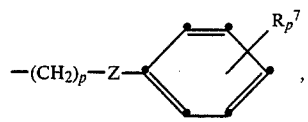

C$_3$–C$_8$ cycloalkyl, 1,3-dioxyl or naphthalenyl;
R$^5$ is

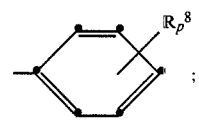

R$^6$ is C$_1$–C$_4$ alkyl, C$_1$–C$_4$ alkoxy, halogen, C$_1$–C$_4$ haloalkyl or C$_1$–C$_4$ haloalkoxy;
R$^7$ is C$_1$–C$_4$ alkyl, C$_1$–C$_4$ alkoxy, C$_1$–C$_4$ alkylthio, halogen, C$_1$–C$_4$ haloalkyl or C$_1$–C$_4$ haloalkoxy;
R$^8$ is C$_1$–C$_4$ alkyl, C$_1$–C$_4$ alkoxy, C$_1$–C$_4$ alkylthio, halogen, C$_1$–C$_4$ haloalkyl, C$_1$–C$_4$ haloalkoxy

Q is O, S or a direct link;
Z is O, S, —CH=CH— or a direct link;
m is 0, 1 or 2;
n is 0, 1, 2 or 3;
each p is 0, 1 or 2;
with the proviso that m and n are not simultaneously 0;
and the agronomically acceptable salts thereof.

2. The method of claim 1 wherein the compound is N-(phenylmethyl)-N-(2,4-dichlorophenyl)-[(3-pyridyl)-methyl]amine.

3. The method of claim 1 wherein the compound is N-(phenylmethyl)-N-(2-chlorophenyl)-[(3-pyridyl)methyl]amine.

4. The method of claim 1 wherein the compound is N-(2,4-dichlorophenyl)-N-[(4-chlorophenyl)methyl]-[(3-pyridyl)methyl]amine.

5. The method of claim 1 wherein the compound is N-(2,4-dichlorophenyl)-N-(naphthalenylmethyl)-[(3-pyridyl)methyl]amine.

6. The method of claim 1 wherein the compound is N-(2,4-dichlorophenyl)-N-(diphenylmethyl)-[(3-pyridyl)methyl]amine.

7. The method of claim 1 wherein the compound is N-butyl-N-(2,4-dichlorophenyl)-[(3-pyridyl)methyl]amine.

8. The method of claim 1 wherein the compound is N-(phenylmethyl)-N-(2,4-difluorophenyl)-[(3-pyridyl]methyl]amine.

9. The method of claim 1 wherein the compound is N-butyl-N-(4-chlorophenyl)-[(3-pyridyl)phenylmethyl]amine.

10. The method of claim 1 wherein the compound is N-(cyclopropylmethyl)-N-(2,4-dichlorophenyl)-[(3-pyridyl)methyl]amine.

11. A compound of the formula

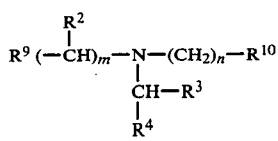

wherein:

R² is hydrogen, $C_1$–$C_6$ alkyl, phenyl or phenyl monosubstituted with $C_1$–$C_4$ alkyl, $C_1$–$C_4$ alkoxy, halogen, $C_1$–$C_4$ haloalkyl or $C_1$–$C_4$ haloalkoxy;

R³ is hydrogen or phenyl;

R⁴ is hydrogen, $C_1$–$C_{12}$ alkyl, $C_1$–$C_{10}$ haloalkyl, $C_2$–$C_{10}$ alkenyl, $C_2$–$C_{10}$ alkynyl,

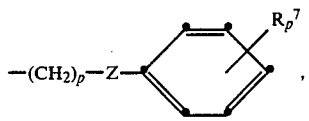

$C_3$–$C_8$ cycloalkyl, 1,3-dioxyl or naphthalenyl;

R⁶ is $C_1$–$C_4$ alkyl, $C_1$–$C_4$ alkoxy, halogen, $C_1$–$C_4$ haloalkyl or $C_1$–$C_4$ haloalkoxy;

R⁷ is $C_1$–$C_4$ alkyl, $C_1$–$C_4$ alkoxy, $C_1$–$C_4$ alkylthio, halogen, $C_1$–$C_4$ haloalkyl or $C_1$–$C_4$ haloalkoxy;

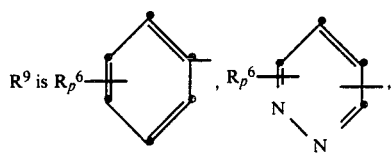

R¹⁰ is

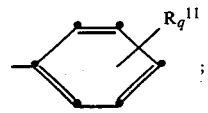

R¹¹ is $C_1$–$C_4$ alkyl, $C_1$–$C_4$ alkylthio, halogen, $C_1$–$C_4$ haloalkyl, $C_1$–$C_4$ haloalkoxy or

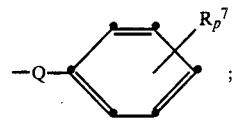

Q is O, S or a direct link;
Z is O, S, —CH=CH— or a direct link;
m is 0, 1 or 2;
n is 0, 1, 2 or 3;
each p is 0, 1 or 2;
q is 1 or 2;
with the proviso that m and n are not simultaneously 0;
and the agronomically acceptable salts thereof.

12. The compound of claim 11 which is N-(phenylmethyl)-N-(2,4-dichlorophenyl)-[(3-pyridyl)methyl]amine.

13. The compound of claim 11 which is N-(phenylmethyl)-N-(2-chlorophenyl)-[(3-pyridyl)methyl]amine.

14. The compound of claim 11 which is N-(2,4-dichlorophenyl)-N-[(4-chlorophenyl)methyl]-[(3-pyridyl)methyl]amine.

15. The compound of claim 11 which is N-(2,4-dichlorophenyl)-N-(naphthalenylmethyl)-[(3-pyridyl)methyl]amine.

16. The compound of claim 11 which is N-(2,4-dichlorophenyl)-N-(diphenylmethyl)-[(3-pyridyl)methyl]amine.

17. The compound of claim 11 which is N-butyl-N-(2,4-dichlorophenyl)-[(3-pyridyl)methyl]amine.

18. The compound of claim 11 which is N-(phenylmethyl)-N-(2,4-difluorophenyl)-[(3-pyridyl)methyl]amine.

19. The compound of claim 11 which is N-butyl-N-(4-chlorophenyl)-[(3-pyridyl)phenylmethyl]amine.

20. The compound of claim 11 which is N-(cyclopropylmethyl)-N-(2,4-dichlorophenyl)-[(3-pyridyl)methyl]amine.

21. A composition comprising an agriculturally-acceptable carrier and a compound of claim 11.

* * * * *

UNITED STATES PATENT AND TRADEMARK OFFICE
CERTIFICATE OF CORRECTION

PATENT NO. : 4,552,960
DATED : November 12, 1985
INVENTOR(S) : Eriks V. Krumkalns and David L. Smiley It is certified that error appears in the above—identified patent and that said Letters Patent is hereby corrected as shown below:

Column 39, lines 38-42, that portion of the formula which reads

"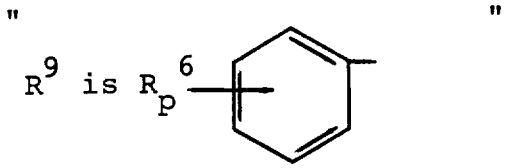"

should read

--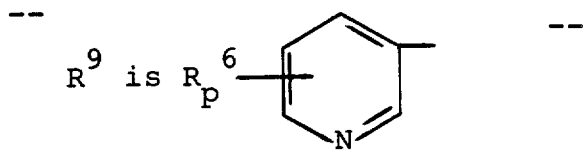--

Signed and Sealed this

Eighth Day of September, 1987

*Attest:*

DONALD J. QUIGG

*Attesting Officer*  *Commissioner of Patents and Trademarks*